United States Patent
Chmielewski

(10) Patent No.: US 6,632,209 B1
(45) Date of Patent: Oct. 14, 2003

(54) THIN ABSORBENT CORE MADE FROM FOLDED ABSORBENT LAMINATE

(75) Inventor: Harry J. Chmielewski, Brunswick, GA (US)

(73) Assignee: Paragon Trade Brands, Inc., Norcross, GA (US)

(*) Notice: Subject to any disclaimer, the term of this patent is extended or adjusted under 35 U.S.C. 154(b) by 441 days.

(21) Appl. No.: 09/685,607

(22) Filed: Oct. 11, 2000

Related U.S. Application Data

(63) Continuation-in-part of application No. 09/676,951, filed as application No. PCT/US99/06805 on Mar. 30, 1999, which is a continuation-in-part of application No. 09/050,003, filed on Mar. 30, 1998, now Pat. No. 6,068,620.

(60) Provisional application No. 60/164,135, filed on Nov. 8, 1999.

(51) Int. Cl.$^7$ .............................................. A61F 13/15
(52) U.S. Cl. ........................ 604/385.101; 604/378; 604/380; 604/385.23; 604/385.01; 604/385.14
(58) Field of Search ...................... 604/378, 385.14, 604/380, 385.101, 385.23, 385.01

(56) References Cited

U.S. PATENT DOCUMENTS

| | | | |
|---|---|---|---|
| 3,667,468 A | * | 6/1972 | Nystrand et al. ............ 604/380 |
| 4,988,344 A | | 1/1991 | Reising et al. |
| 5,176,672 A | * | 1/1993 | Bruemmer et al. ...... 604/385.01 |
| 5,304,161 A | * | 4/1994 | Noel et al. .................... 604/378 |
| 5,462,541 A | * | 10/1995 | Bruemmer et al. .......... 604/391 |
| 5,506,277 A | | 4/1996 | Griesbach, III |
| 5,569,228 A | | 10/1996 | Byrd et al. |
| 5,672,418 A | | 9/1997 | Hansen et al. |
| 6,068,620 A | | 5/2000 | Chmielewski |

* cited by examiner

Primary Examiner—Rodney M. Lindsey
Assistant Examiner—Angela J Grayson
(74) Attorney, Agent, or Firm—Hunton & Williams

(57) ABSTRACT

A disposable absorbent garment comprising a topsheet, a back-sheet and an absorbent core disposed between the topsheet and backsheet is disclosed. The absorbent core is formed from a folded laminated comprising three layers, including an upper layer, a lower layer and a central fibrous layer including from about 50 to about 95 percent by weight superabsorbent polymer and about 5 to about 50 percent by weight stabilization additives. The upper and lower layers comprise tissue, airlaid fluff pulp synthetic non-woven fibrous layers. The central fibrous layers is adhesively bonded to both the upper and lower layers, all layers together assisting to maintain the dry and wet integrity of the absorbent core. Folding of the thin absorbent laminate provides an absorbent core that can handle large doses of urine. The folded structure provides a central channel that provides free volume for temporary liquid storage, isolation and containment of bowel movements, and increases the surface area of laminate available for liquid absorption. The absorbent garment thus formed is very thin, lightweight and economical.

33 Claims, 14 Drawing Sheets

THIN ABSORBENT CORE MADE FROM FOLDED ABSORBENT LAMINATE

RELATED APPLICATIONS

This application claims priority to U.S. Provisional Patent Application Serial No. 60/164,135, filed Nov. 8, 1999, and is a continuation-in-part of U.S. patent application Ser. No. 09/676,951, filed on Oct. 2, 2000, which is the U.S. national phase of PCT/US99/06805, filed Mar. 30, 1999, which is a continuation-in-part of Ser. No. 09/050,003, U.S. Pat. No. 6,068,620, filed Mar. 30, 1998, all of which are incorporated herein by reference.

FIELD OF THE INVENTION

The present invention relates generally to absorbent garments. Particularly, it relates to thin, folded, "pulpless" absorbent cores for disposable absorbent garments having improved core integrity in-use, high SAP efficiency, high surge capacity, and bowel movement containment ability.

BACKGROUND OF THE INVENTION

Traditionally, disposable absorbent garments, such as infant diapers or training pants, adult incontinence products and other such products, are constructed with a moisture-impervious outer backing sheet (or "backsheet"), a moisture-pervious body-contacting inner liner sheet (or "topsheet"), and a moisture-absorbent core (or "absorbent core") sandwiched between the liner sheet and the backing sheets.

Much effort has been expended to find cost-effective materials for absorbent cores which display good liquid absorbency and retention. Superabsorbent polymers or superabsorbent materials in the form of granules, beads, fibers, bits of film, globules, etc., have been favored for such purposes. Such superabsorbent materials are generally polymeric gelling materials which are capable of absorbing and retaining even under moderate pressure large quantities of liquid, such as urine and body wastes, relative to their weight. The term "superabsorbent polymer" is often abbreviated as "SAP."

The superabsorbent material is generally a water-insoluble but water-swellable polymeric substance capable of absorbing water in an amount which is at least ten times the weight of the substance in its dry form. In one type of superabsorbent material, the particles or fibers may be described chemically as a crosslinked, sodium-neutralized polyacrylate. Included in this class of materials are such modified polymers as sodium-neutralized crosslinked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be crosslinked to reduce their water solubility.

The ability of a superabsorbent material to absorb liquid is dependent upon the form, position and/or manner in which particles of the superabsorbent material are incorporated into the absorbent core. Whenever the superabsorbent material in the absorbent core is wetted, it swells and forms a gel. Gel formation can block liquid transmission into the interior of the absorbent core, a phenomenon called "gel blocking". Gel blocking prevents liquid from rapidly flowing or wicking past the "blocking" particles of superabsorbent, causing portions of a partially hydrated core to become inaccessible to multiple doses of liquids, such as urine, water and saline solutions. Further absorption of liquid by the absorbent core must then take place via a diffusion process within the polymer gel. This is typically much slower than the rate at which liquid is applied to the core. Gel blocking often leads to leakage from the absorbent article well before all of the absorbent material in the core is fully saturated.

Despite the incidence of gel blocking, superabsorbent materials are commonly incorporated into absorbent cores because they absorb and retain large quantities of liquid, even under load. However, in order for superabsorbent materials to function, the liquid being absorbed in the absorbent structure must be transported to unsaturated superabsorbent material. In other words, the superabsorbent material must be placed in a position to be contacted by liquid. Furthermore, as the superabsorbent material absorbs the liquid, it must be allowed to swell so as to maintain a capillary structure within the absorbent core to distribute liquid.

Adequate absorbency of liquid by the absorbent core at the point of initial liquid contact and rapid distribution of liquid away from this point is necessary to ensure that the absorbent core has sufficient capacity to absorb subsequently deposited liquids. Prior art absorbent cores have thus attempted to absorb quickly and distribute large quantities of liquids throughout the absorbent core while minimizing gel blocking during absorption of multiple doses of liquid.

In general, some of the most important performance attributes of an absorbent core of a diaper (or any other absorbent garment) are functional capacity, rate of absorption, and core stability in use. Absorption under load or AUL of the core is a good measure of functional capacity and the rate at which that absorption occurs. Core AUL is a function of both SAP basis weight (mass of SAP per unit area), physical properties or AUL of the SAP, and absorbency of other materials used in the core. Baby diaper cores that contain only fluff pulp and a high gel strength SAP maintain adequate functional absorbency and SAP efficiency if the core contains less than about 50 percent SAP. Fluff/SAP diaper cores containing more than 50 percent SAP by weight result in lower functional absorbency because of gel blocking. Although fluff/SAP cores at greater than 50 percent SAP can provide adequate absorbency, the overall basis weight of the core must be increased to compensate for the lower efficiency of the SAP. Increasing the basis weight decreases the performance/cost ratio of the absorbent core, making them uneconomical. Also, increased basis weights tend to affect the fit and comfort of the garment, as well as impacting unfavorably packaging and shipping costs.

Another desirable performance attribute of an absorbent core of a disposable diaper, training pant, incontinence garment, or the like, is the ability of the absorbent core to isolate and contain bowel movements away from the user's skin. However, in the past, bowel movement containment features have involved the use of complex pouches, spacers, and folding schemes that add significant bulk to the absorbent garment, and require significant increases in raw material consumption and/or development of complex manufacturing processes.

The comfort, fit and wearability of a diaper is greatly improved by reducing the thickness of the absorbent core. However, absorbent articles having thin absorbent cores are generally much less effective than absorbent articles having thick absorbent cores. Thin, "pulpless" absorbent cores generally suffer from poor core stability in-use, poor bowel movement containment ability, poor SAP efficiency due to gel blocking and low absorption rate (or surge capacity).

Therefore, it is highly desirable to provide an absorbent article with a thin, pulpless, absorbent core having improved core stability in-use, bowel movement containment ability, SAP efficiency and absorption rate. Garments made from such thin absorbent cores would also exhibit improved comfort, fit and wearability without sacrificing the liquid absorption characteristics of the absorbent article.

The present invention as defined by the preferred embodiments is designed to overcome the foregoing and other deficiencies of prior art absorbent garments while providing a thin absorbent core made from a folded absorbent laminate.

SUMMARY OF THE INVENTION

It is therefore an object of the invention to provide a thin absorbent garment having an improved ability to retain fluids.

It is a further object of the invention to provide an absorbent garment having an improved ability to isolate and contain bowel movements away from the user's skin.

It is another object of the invention to provide an absorbent garment having improved comfort, fit and wearability.

It is yet another object of the invention to provide an absorbent garment having a thin absorbent core.

It is a further object of the invention to provide an absorbent garment with a pulpless absorbent core having SAP as a substantial percentage of its basis weight, generally greater than 50%, the absorbent core being substantially free of gel blocking, i.e., the core retaining high SAP efficiency.

It is still yet a further object of the invention to provide an absorbent garment with an absorbent core having high dry and wet strength for processing and in-use performance.

It is still yet a further object of the invention to provide a thin, high density absorbent laminate or composite having good liquid absorption characteristics and especially surge capacity or absorption rate.

It is yet a further object of the invention to provide an absorbent core comprising one or more laminates wherein one of the layers of the laminate or laminates is a high-density, high SAP-containing layer.

These and other objects of the invention are achieved by a disposable absorbent article comprising a thin, folded, pulpless absorbent core. Preferably, the absorbent core includes a laminate structure (or an "absorbent laminate" or "laminate" or a "composite") comprising an absorbent layer sandwiched between an upper tissue layer and a lower tissue layer. Preferably, the upper layer has high liquid porosity and the lower layer has a high wet strength. The absorbent layer comprises fibrous or particulate additives or materials or a mixture of the fibrous and particulate additives that are effective for maintaining high SAP efficiency. These additives or materials will hereinafter be referred to as "SAP stabilization additives or materials," "stabilization additive or materials" or "SAP efficiency additives or materials." They generally allow for an efficient utilization of the SAP material at high SAP concentrations. Typically, prior art absorbent cores at SAP concentrations greater than about 50 percent by weight exhibited SAP efficiencies of less than about 70 percent. Pulpless absorbent cores according to preferred embodiments of the invention, having SAP concentrations from about 50 to about 95 percent by weight, exhibit SAP efficiencies of at least about 70 percent, preferably greater than about 80 percent and more preferably greater than about 90 percent. Preferably, the SAP material is dispersed substantially homogeneously within a continuous matrix of the fibrous or particulate additives (or their mixture). More preferably, the SAP material should form a substantially continuous phase and the fibrous or particulate material (or their mixture) is dispersed within the voids formed between the SAP material.

The SAP stabilization additives in combination with a careful selection of adhesives and application patterns of the adhesives minimize gel blocking. Moreover, the adhesives and adhesive patterns employed in the preferred embodiments of this invention selectively modify the porosity of the upper and lower tissue layers (of the laminate) and improve the overall absorbent core integrity in use.

The fibrous or particulate additives are used at an effective amount for maintaining high SAP efficiency even at high SAP concentrations. Fibrous additives preferably include cellulose acetate fibers, rayon fibers, lyocell fibers, polyacrylonitrile fibers, surface-modified (hydrophilic) polyester fibers, surface-modified polyolefin/polyester bicomponent fibers, surface-modified polyester/polyester bicomponent fibers, polypropylene fibers, other olefin fibers, cotton fibers, cotton linters or blends thereof. Preferred particulate additives include potato, corn, wheat, and rice starches.

The absorbent core according to the preferred embodiments of the present invention includes an absorbent layer having an average density of from about 0.10 to about 0.40 grams per cubic centimeter, preferably from about 0.15 to about 0.35 grams per cubic centimeter, and most preferably about 0.20 to about 0.30 grams per cubic centimeters. Also the thickness of preferred absorbent layers is less than about 0.5–1.1 millimeters, preferably from about 0.6 to about 1.0 millimeters, and more preferably from about 0.75 to about 0.85 millimeters.

Finally, the folded structure of the absorbent core exhibits substantially improved liquid absorption rate or surge capacity as compared to conventional pulp/SAP cores containing about 35–50% SAP. Preferably, the absorbent core is folded so as to form a longitudinally extending central channel between side folded areas. Such a central channel provides for the isolation and containment of bowel movements within the absorbent core and away from the user's skin. It is postulated without wishing to limit the invention in any way that the improved absorption rate and bowel movement containment of the folded structure is generally associated with the increased free volume and surface area of the folded core. In addition to the foregoing advantages, absorbent garments having absorbent cores according to the present invention exhibit improved comfort, fit and wearability of the garment. Such absorbent garments or articles include a liquid permeable topsheet, a liquid impermeable backsheet and the folded absorbent core of this invention. Further, due to the relatively low thickness of the resulting product, less packaging material is needed for the same amount of product, which in turn results in lower shipping and handling costs.

These and other objects, features and advantages of the preferred embodiments will become more readily apparent upon reading of the detailed description of the preferred embodiments of this invention in conjunction with the following drawings.

DETAILED DESCRIPTION OF THE PREFERRED EMBODIMENTS

Figure 1:
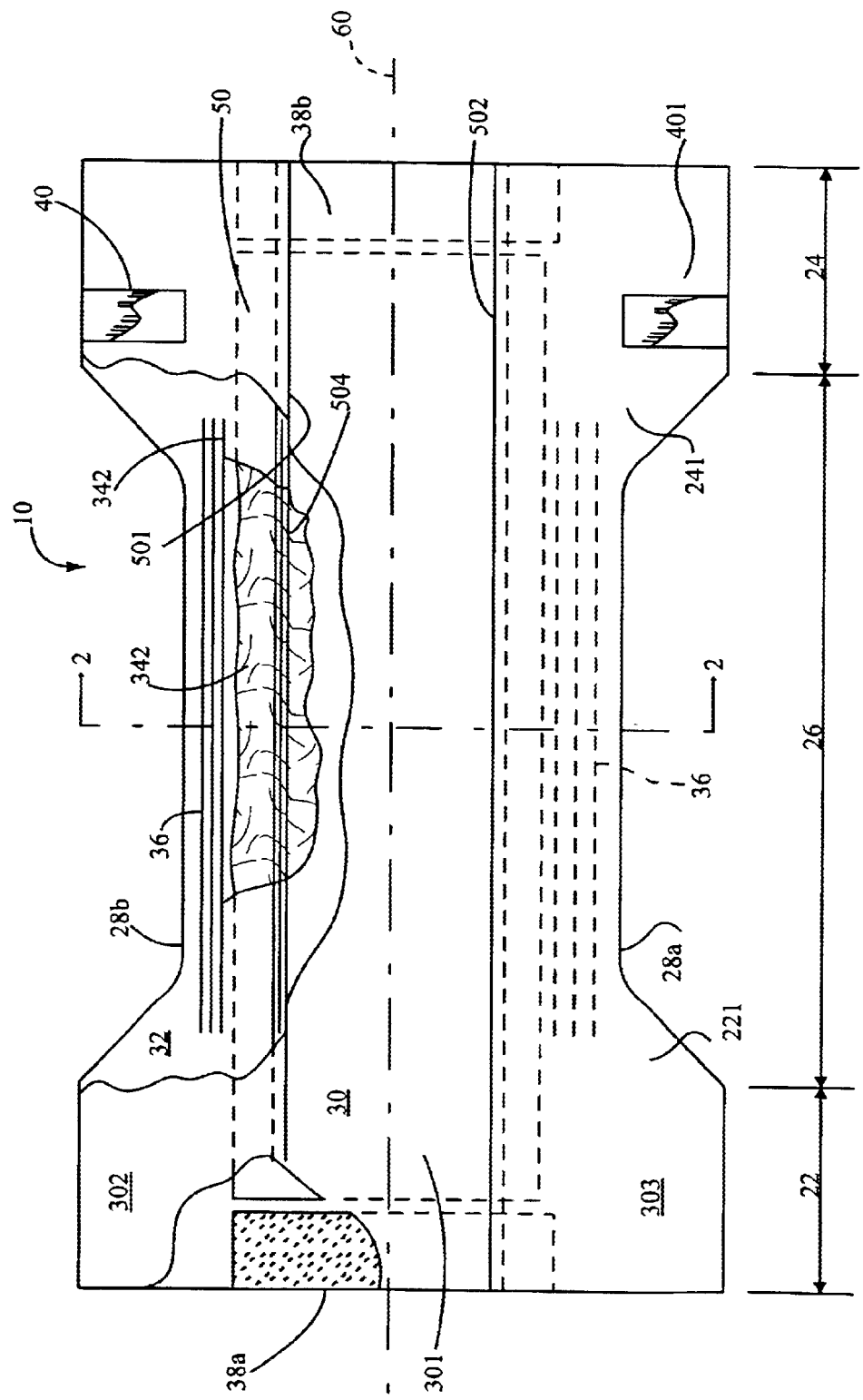
FIG. 1 is a plan view of an absorbent garment incorporating an absorbent core according to a preferred embodiment of the invention with the effects of the elastics of the garment removed.

As used herein, the term "absorbent garment" or "absorbent article" refers to garments that absorb and contain exudates, and more specifically, refers to garments which are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. The term "disposable absorbent garment" refers to absorbent garments that are intended to be discarded or partially discarded after a single use (i.e., they are not intended to be laundered or otherwise restored or reused). The term "unitary disposable absorbent garment" refers to a disposable absorbent garment that is essentially a single structure (i.e., it does not require separate manipulative parts such as a diaper cover and insert). As used herein, the term "diaper" refers to an absorbent garment generally worn by infants and incontinent persons about the lower torso.

The absorbent core of the preferred embodiments can be used with all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes and types of absorbent garments, including those described above.

Preferably, the absorbent core is thin, preferably less than about 3 mm (in the folded region, discussed more fully below) in order to improve the comfort and appearance of the garment. The importance of thin, comfortable garments is disclosed in U.S. Pat. No. 5,098,423 to Pieniak et al., which is herein incorporated by reference for all purposes and in a manner consistent with the present invention.

Generally, the absorbent core is formed from a very thin, high density, folded absorbent laminate that contains superabsorbent polymer (SAP) and stabilization additives. Preferably, the SAP and the stabilization additives are included in an absorption layer, which is sandwiched between an upper layer of highly porous, liquid permeable material (the "upper layer") and a lower layer of a high wet strength material (the "lower layer") that can be made substantially liquid impervious by application of a nearly coherent film of adhesive, i.e., at a high adhesive coverage.

The absorbent layer comprises from about 50 to about 95 percent by weight, preferably from about 60 to about 95 percent by weight, and more preferably from about 70 percent to about 90 percent by weight SAP. The absorbent layer also comprises an effective amount of at least one fibrous or particulate additive for maintaining a high SAP efficiency of the absorbent core of at least about 70 percent, preferably at least about 80 percent, and more preferably at least about 85 percent.

The folded structure of the absorbent core is formed by folding at least once the marginal sides of the absorbent core to form a central channel extending longitudinally along the absorbent core. The folding provides a three-dimensional structure to the absorbent core. The folded absorbent core has a central channel area formed between two side folded areas. It is believed, without wishing to limit the invention, that the central channel and the space between the foldings in the side-folded areas increase the free volume that is available for temporarily containing large doses of liquid such as urine and body wastes, until they can be absorbed by the SAP in the laminate. The folded structure of the absorbent core also significantly increases the effective surface area of laminate that is available for liquid absorption.

The upper and lower layers of the absorbent laminate are preferably made from tissue material, synthetic fiber webs, or airlaid fluff pulp. The upper and lower layers are preferably made from separate pieces of different material, although the upper and lower layers can be made from one (folded) or two pieces of the same material. Preferably, the upper layer has an effective porosity for allowing the easy passage of liquid into the absorbent layer and for preventing the migration of SAP into the topsheet area of the diaper. The lower layer is preferably rendered substantially liquid impervious by the application of adhesive and generally has a higher wet strength than the upper layer. In a particularly preferred embodiment, the porosities of the upper and lower layers of the absorbent laminate are modified through adhesive selection and application.

Porosity is defined as the time it takes for 100 ml of 0.9% saline solution to penetrate through a circular portion of the absorbent layer being 2 inches in diameter and is expressed in units of $ml/cm^2/min$. Preferably, the upper layer has a (high) porosity of greater than about 30 $ml/cm^2/min$, and preferably greater than about 40 ml/cm$^2$/min. Preferably the lower layer has a (low) porosity of less than about 10 ml/cm$^2$/min, and more preferably less than about 5 ml/cm$^2$/min. In the most preferred embodiment, adhesive is added to the lower layer to render it substantially non-porous or liquid impermeable. Preferably the lower layer has a wet machine direction (MD) tension strength of at least about 150 gm/inch, and more preferably of at least about 200 gm/inch.

The type and amount of adhesive, as well as the method of applying it, affect the porosity of the upper layer and the lower layer and the amount of SAP that can be bonded to these layers. It is important to maximize porosity of the upper layer. Generally, the absorbent layer is attached to the upper layer using a low basis weight hydrophilic or hydrophobic, but preferably hydrophilic, adhesive at the interface between the absorbent layer and the upper layer. Preferably, less than about 2, and more preferably about 1.6, grams per square meter (g/sm) of a hydrophilic adhesive is applied at low coverage to the upper layer using, for example, Nordson (Norcross, Ga.) CONTROLLED FIBERIZATION™ or ITW Dynatec (Hendersonville, Tenn.) DYNAFIBER™ UFD-5 adhesive spray nozzles utilizing relatively low air pressures (less than 5 psi) to allow for a large diameter adhesive fibers and more open area. More preferably, H2561, a hydrophilic construction adhesive having a resin ester tackifier, and H2594, a hydrophilic construction adhesive having a hydrocarbon tackifier, are used. These adhesives are made by AtoFindley, located in Wauwatosa, Wis.

The adhesive on the lower layer promotes SAP entrapment, permits selective modification of tissue porosity, and attaches the lower layer to the absorbent layer. Selective modification of tissue porosity is achieved by spraying a center area of the lower layer with preferably more than about 2–8 g/sm, and more preferably about 6 g/sm, of a hydrophilic adhesive at high coverage from, for example, a CONTROL COAT™ or DYNAFIBER™ UFD-17 spray nozzle. Preferably, there are different degrees of adhesive application on the lower layer. The central portion of the lower layer has a higher basis weight application and higher coverage as compared with the outer lateral portions thereof. This is due to the fact that the outer portions of the lower layer are folded to form a portion of the upper surface of the absorbent core. That is, upon folding, the outer portions of the lower tissue layer form the outer, top portion of the core. Consequently, outside of the center portion of the lower layer, a lower amount of adhesive, preferably less than about 5 g/sm, is applied at lower coverage using, for example, CONTROL WEAVE™ or DYNAFIBER™ UFD-13 adhesive nozzles, to maintain adequate porosity for a portion of the lower tissue that will reside on the upper surface of the folded core.

The absorbent core may contain more than one absorbent laminates. Forming the absorbent core with one or more laminates decouples key performance characteristics of the absorbent core. This concept is described in detail in the parent application, Ser. No. 09/050,003 by the same inventor and entitled "Absorbent Laminate," which is herein incorporated by reference for all purposes and in a manner consistent with this application and invention. However, at least one of the laminates in the absorbent core laminate is a thin, folded, pulpless absorbent laminate having high SAP efficiency.

SAP efficiency is a measure of the effectiveness of the SAP in the laminate and is the ratio, expressed as a percentage, of the actual SAP absorbency under load at a given pressure, or AUL (expressed as grams of saline absorbed per gram of SAP in the laminate), and the maximum SAP AUL obtained under ideal conditions of absorption where the SAP AUL is independent of SAP basis weight.

In a preferred embodiment, the spreading of liquid in the disposable absorbent article can be enhanced by replacing the upper layer of the absorbent core with a material that can function as an internal spreading layer or by adding a separate internal spreading layer that can be cut and placed in the front of the absorbent core (or "absorbent laminate"), i.e., on top of the upper layer.

The present invention is premised in part on the unexpected discovery that certain fibrous and particulate materials or additives also referred to as "stabilization additives" or "SAP efficiency additives" are effective in maintaining high SAP efficiency when the SAP concentration in the absorbent core is greater than about 50 percent by weight. Without limiting the scope of the invention, it is postulated that these fibrous and particulate materials stabilize the SAP material and prevent the gelling phenomenon that marred prior art absorbent cores. The fibrous or particulate additives are employed in an amount effective to maintain high SAP efficiencies of at least about 70 percent, preferably greater than about 80 percent and most preferably equal to or greater than about 90 percent. SAP concentrations range from about 50 to about 95 percent, preferably about 60 to about 90 percent, and more preferably from about 75 to about 85 percent.

Super absorbent polymers having cross-linked surfaces perform best in these laminates. U.S. Pat. No. 5,147,343 issued to Kellenberger, U.S. Pat. No. 4,673,402 issued to Weisman, U.S. Pat. No. 5,281,207 issued to Chmielewski et al., and U.S. Pat. No. 4,834,735 issued to Alemany, et al. disclose many types of SAPs and methods for making them, and are incorporated herein by reference for all purposes and in a manner that is consistent herewith. Surface crosslinked SAPs and methods of making them are described in U.S. Pat. Nos. 4,666,983 and 4,734,478 issued to Tsubakimoto et al., which are incorporated herein by reference for all purposes and in a manner that is consistent herewith. Also, U.S. Pat. No. 5,281,207 to Chmielewski, et al. generally discloses methods and materials for making an absorbent article and is also incorporated herein by reference for all purposes and in a manner that is consistent herewith.

These fibrous and/or particulate additives are preferably constituent elements of the absorbent layer of the laminate. Fibrous additives preferably include cellulose acetate fibers, rayon fibers, lyocell fibers, polyacrylonitrile fibers, surface-modified (hydrophilic) polyester fibers, surface-modified polyolefin/polyester bicomponent fibers, surface-modified polyester/polyester bicomponent fibers, polypropylene fibers, other olefin fibers, cotton fibers, cotton linters or blends thereof. More preferably, the fibrous additives include rayon fibers, lyocell fibers, polyacrylonitrile, cotton fibers and cotton linters. Of the foregoing, cellulose acetate is the most preferred fibrous additive because of its superior liquid handling properties (i.e., wicking, absorbent capacity, and resistance to wet collapse). Cellulose acetate fiber is also available in a compact tow form that is advantageous for high speed, continuous converting of absorbent products. Generally to maintain high SAP efficiencies at high SAP concentrations, the concentration of fibrous additives in the absorbent layer of the absorbent laminate should preferably be from about 5 to about 50 percent, and more preferably from about 10 to about 30 percent, and most preferably from about 15 to about 25 percent. Most preferably, the absorbent layer comprises from about 75 to about 85 percent SAP and from about 15 to about 25 percent fibrous additives.

In a preferred embodiment, the cellulose acetate is in the form of a tow. Cellulose acetate (CA) tows are continuous lengths of highly crimped fibers which are compressed in bales. Commercially available CA tows can be pulled from the bale and can be effectively opened at high speeds. "Opening" is the process of separating filaments from one another to increase tow volume. SAP material is combined with the open CA tow and compressed between the upper and lower layers to form an absorbent laminate. Of course, other fibrous additives may also be used in the form of a tow.

Particulate additives may also be added to the absorbent layer in addition to or as a substitute for the foregoing fibrous additives in order to maintain SAP efficiency. Suitable particulate additives generally include water insoluble, hydrophilic polymers with particle diameters of less than about 200 $\mu$m. Particles of hydrophobic polymers can also be used by subjecting them to well known chemical or physical treatments in order to render their surface hydrophilic. Both organic and inorganic, hydrophilic and polymeric materials can be used. Preferably, the particulate additives are insoluble, hydrophilic polymers with particle diameters of less than about 500 $\mu$m, preferably less than about 300 $\mu$m, and more preferably less than about 100 $\mu$m. The particulate additives may be of many different shapes, but preferably are irregularly shaped to provide for maximum free volume for a given particle size. Generally, the particulate additives are chosen to impart a capillary network to the partially hydrated, SAP-containing absorbent layer to improve SAP efficiency.

Preferred particulate additives include potato, corn, wheat, and rice starches. Partially cooked or chemically modified (i.e., modifying hydrophobicity, hydrophilicity, softness, and hardness) starches can also be effective in keeping the SAP particles separated, thereby maintaining the efficiency of SAP. Most preferably, the particulate additives comprise partially cooked corn or wheat starch because in this state, the corn or wheat are rendered larger than uncooked starch and even in the cooked state remain harder than even swollen SAP.

Fibrous and particulate additives can be used together in the absorbent laminate. Some examples of absorbent layer compositions include:

| Material | % Basis Weight | | | | |
| --- | --- | --- | --- | --- | --- |
| | Example A | Example B | Example C | Example D | Example E |
| SAP | 90% | 90% | 80% | 80% | 60% |
| Fiber | 0% | 10% | 20% | 10% | 20% |
| Particulate | 10% | 0% | 0% | 10% | 20% |

Moreover, it has been unexpectedly discovered that a thin absorbent core can be made having excellent absorption rates (or surge capacity) by longitudinally folding the marginal sides of the absorbent core to form a central channel between the side foldings. Without wishing to be bound by any theory of operability, it is believed that the channel and the space between the folded layers of the side foldings provide free temporary storage space for the liquids before the SAP material can absorb them. In addition, the absorbent cores of the present invention exhibit excellent in-use core stability.

For simplicity, some of the preferred embodiments of the invention will be described in terms of a disposable absorbent garment 10, i.e., a diaper, such as shown in FIG. 1. Of course, it should be understood, however, that the present invention is applicable to other types of absorbent garments and absorbent articles. Thus, the description of unique features of the invention in conjunction with a diaper is equally applicable to the use of the invention with other types of absorbent garments and articles.

With reference to FIG. 1, the diaper 10 according to a preferred embodiment is shown in a relaxed condition with the effects of the elastics removed for purposes of clarity in description. The diaper 10 has a generally hourglass shape and can generally be defined in terms of a front waist region 22, a back waist region 24, and a crotch region 26. Alternatively, the diaper can be configured in a generally rectangular shape or in a "T" shape. A pair of leg openings 28a, 28b extend along at least a portion of the crotch region 26. The diaper preferably comprises a topsheet 30, a backsheet 32, which may be substantially coterminous with the topsheet 30, and an absorbent core laminate 342 disposed between at least a portion of the topsheet 30 and the backsheet 32. One or more pairs of leg elastics 36 (three pairs are shown in FIG. 1) extend adjacent to leg openings 28a, 28b, respectively.

The diaper may further include a front waist elastic system 38a, a back waist elastic system 38b, a fastening system 40 (e.g., tape or other suitable mechanical fastener) and a waste containment system 50 in the form of waste containment flaps 501, 502. Waste containment flaps 501, 502 preferably extend from the front waist region 22 to the back waist region 24 along opposite sides of a longitudinal center line or axial center line 60 of the diaper 10, or alternatively only along a portion thereof.

The front waist region 22 and rear waist region 24 include ear portions 221, 241 extending outwardly from the leg openings 28a, 28b. The waist elastics 38a, 38b may be structures similar to each other or different to impart similar or different elastic characteristics to the front and back waist portions of the diaper. In general, the waist elastics may comprise foam strips positioned at the front and back waist sections 22, 24. The foam strips are preferably about ½ to 1½ inches wide and about 3–6 inches long. The foam strips are preferably positioned between the topsheet 30 and the backsheet 32. Alternatively, a plurality of elastic strands may be employed as waist elastics rather than foam strips. The foam strips are preferably made from polyurethane, but could be made of any other suitable material which decreases waist band rollover, reduces leakage over the waist ends of the absorbent garment, and generally improves comfort and fit. The front and back waist elastics (or foam strips) 38a, 38b are stretched from about 50 to about 150 percent, preferably about 100 percent before being adhesively secured between the backsheet 32 and the topsheet 30.

Due to the wide variety of backing and liner sheet construction and materials currently available, the invention is not intended to be limited to any specific materials or constructions of these components. The backsheet 32 is made of any suitable pliable liquid impervious material known in the art. Typical backsheet materials include films of polyethylene, polypropylene, polyester, nylon, and polyvinyl chloride and blends of these materials. For example, the backsheet can be of a pigmented polyethylene film having a thickness in the range of 0.02–0.04 mm. The moisture-pervious topsheet 30 can be made of any suitable relatively liquid-pervious material known in the art that permits passage of a liquid therethrough. Non-woven liner sheet materials are exemplary because such materials readily allow the passage of liquids to the underlying absorbent core 342. Examples of suitable liner sheet materials include non-woven spunbond or carded webs of polypropylene, polyethylene, nylon, polyester and blends of these materials.

The back-sheet 32 and the topsheet 30 are "associated" with one another. The term "associated" encompasses configurations whereby the topsheet 30 is directly joined to the back-sheet 32 by affixing the topsheet 30 directly to the backsheet 32, and configurations whereby the topsheet 30 is indirectly joined to the backsheet 32 by affixing the topsheet 30 through intermediate members, which in turn are affixed to the backsheet 32. While the backsheet 32 and topsheet 30 in the preferred embodiment have substantially the same dimensions, they may also have different dimensions.

In addition, the backsheet 32 may be covered with a fibrous, nonwoven fabric (i.e., a fibrous outer liner) such as is disclosed for example in U.S. Pat. No. 4,646,362, which is hereby incorporated by reference and in a manner consistent with the present application and invention. Materials for such a fibrous outer liner include a spun-bonded nonwoven web of synthetic fibers such as polypropylene, polyethylene or polyester fibers; a nonwoven web of cellulostic fibers, textile fibers such as rayon fibers, cotton and the like, or a blend of cellulostic and textile fibers; a spun-bonded nonwoven web of synthetic fibers such as polypropylene, polyethylene or polyester fibers mixed with cellulostic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulostic, pulp or textile fibers. Alternatively, the backsheet may comprise three panels wherein a central backsheet panel is positioned adjacent the absorbent core while outboard non-woven breathable side backsheet panels are attached to the side edges of the central backsheet panel. Alternatively, the back-sheet may be formed from microporous coverstock for added breathability.

Figure 2:
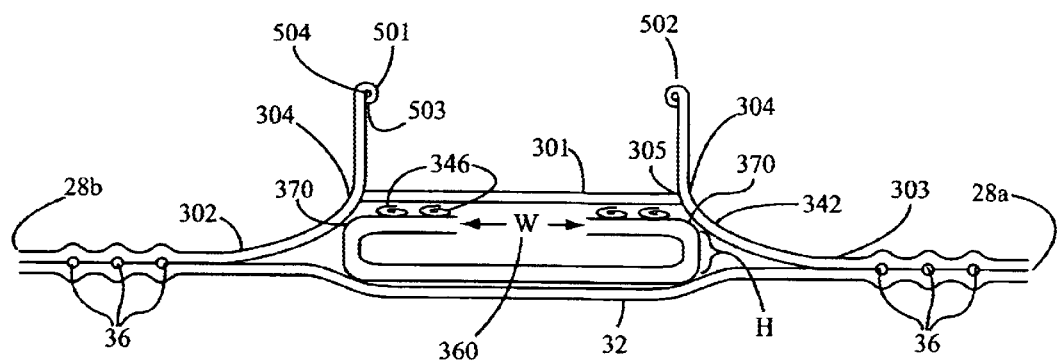
FIG. 2 is a cross-section of the absorbent garment taken along line 2—2 of FIG. 1 illustrating one preferred embodiment of the absorbent core laminate.
Figure 3:
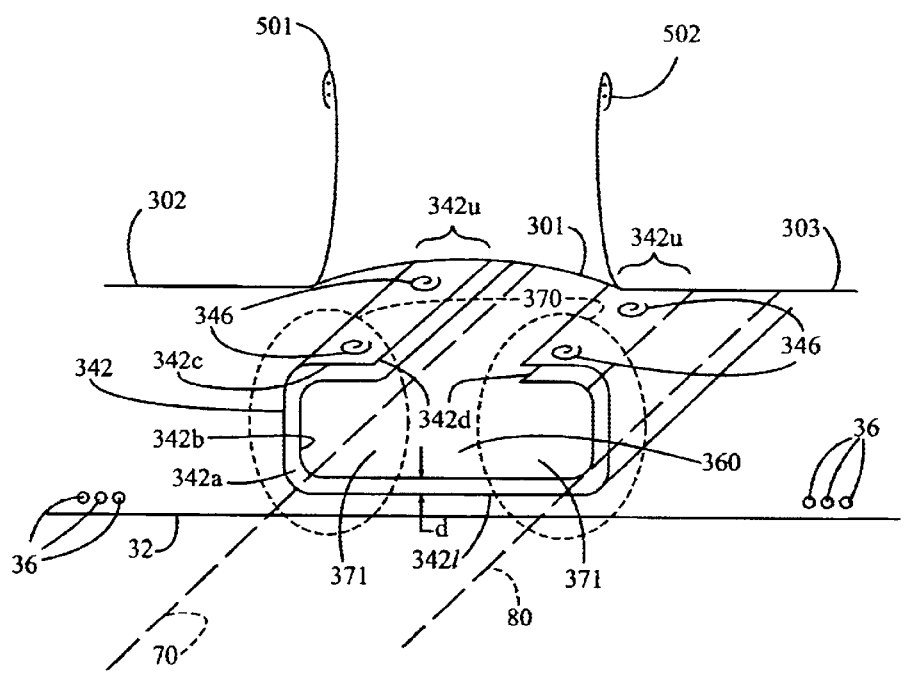
FIG. 3 is an exploded partial cross-sectional schematic perspective view of the absorbent garment of FIG. 2.

Alternatively, the topsheet may be formed of three separate portions or panels as shown in FIGS. 2 and 3. A first central topsheet panel 301 may comprise a central topsheet panel formed from preferably a liquid-pervious material that is either hydrophobic or hydrophilic. The central topsheet panel 301 may be made from any number of materials, including synthetic fibers (e.g., polypropylene or polyester fibers), natural fibers (e.g., wood or cellulose), apertured plastic films, reticulated foams and porous foams to name a few. One preferred material for a central topsheet panel 301 is a cover stock of single ply nonwoven material which may be made of carded fibers, either adhesively or thermally bonded, perforated plastic film, spunbonded fibers, or water entangled fibers, which generally weigh from 0.3–0.7 oz./sq. yd. and have appropriate and effective machine direction and cross-machine direction strength suitable for use as a baby diaper cover stock material. The central topsheet panel 301 preferably extends from substantially the front waist region 22 to the back waist region 24 or a portion thereof.

The second and third marginal (or outer) topsheet panels 302, 303 in this alternative embodiment may be positioned laterally outside of the central topsheet panel 301. The outer topsheet panels 302, 303 are preferably substantially liquid-impervious and hydrophobic, preferably at least in the crotch area. The outer edges of the outer topsheet panels may substantially follow the corresponding outer perimeter of the backsheet 32. The material for the outer topsheet portions or panels is preferably polypropylene and can be woven, non-woven, spunbonded, carded or the like, depending on the application.

The inner edges 304 (FIG. 2) of the outer topsheet portions or panels 302, 303 preferably are attached by any suitable means (e.g., an adhesive) to the outer edges 305 of the inner topsheet portion or panel 301. At the point of connection with the outer edges 305 of the inner topsheet portion or panel 301, the inner edges 304 of the outer topsheet portions or panels 302, 303 extend upwardly to form waste containment flaps 501, 502. The waste containment flaps 501, 502 are preferably formed of the same material as the outer topsheet portions or panels 302, 303, as in the embodiment shown. They are preferably an extension of the outer topsheet portions or panels 302, 303.

The waste containment flaps 501, 502 may be treated with a suitable surfactant to modify their hydrophobicity/hydrophilicity as desired. Alternatively, the waste containment flaps 501, 502 may be formed as separate elements and then attached to the body side liner. In this alternative embodiment, the central topsheet portion or panel 301 may extend past the connection point with the waste containment flaps 501, 502, and even extend to the periphery of the backsheet. Still further, the central topsheet portion or panel 301 could extend fully between the outer topsheet portions or panels 302, 303 and even beyond so that the outer edges 305 of the central topsheet portion or panel 301 are coextensive with and sandwiched between the outer topsheet portions or panels 302, 303 and the backsheet 32.

The waste containment flaps 501, 502 preferably include a portion 503 which folds over onto itself to form a small enclosure. At least one, and depending on the size of the enclosure, sometimes more than one, elastic member 504 (FIG. 2) is secured in the small enclosure in a stretched condition. As has been known at least as long the disclosure of Tetsujiro, Japanese Patent document 40-11543, when the flap elastic 504 attempts to assume the relaxed, unstretched condition, the waste containment flaps 501, 502 rise above the surface of the central topsheet portion or panel 301.

In any or all of the foregoing embodiments, the topsheet may comprise a single sheet of a material including portions of different characteristics (e.g., liquid-imperviousness/perviousness and/or hydrophobicity/hydrophilicity) and have regions of transition or demarcation therebetween.

Each leg opening 28a, 28b is provided with a leg elastic containment system 36. In the preferred embodiment, three strands of elastic threads are positioned to extend adjacent to leg openings 28a, 28b between the outer topsheet portions or panels 302, 303 and the backsheet 32. Any suitable elastomeric material exhibiting at least an elongation (defined herein as $(L_s-L_R)/L_R$; where $L_s$ is the stretched length of an elastic element and $L_R$ is retracted length, multiplied by 100 to obtain percent elongation) in the range of about 50 percent to about 350 percent, preferably in the range of about 200 to about 300 percent, can be employed for the leg elastics 36. The leg elastics 36 may be attached to the diaper 10 in any of several ways which are known in the art. For example, the leg elastics 36 may be ultrasonically bonded, heat/pressure sealed using a variety of bonding patterns, or glued to the diaper 10.

Various commercially available materials can be used for the leg elastics 36, such as natural rubber, butyl rubber or other synthetic rubber, urethane, elastomeric materials such as LYCRA (DuPont), GLOSPAN (Globe) or SYSTEM 7000 (Fulflex).

The fastening system 40 of the preferred embodiment is attached to the back waist region 24, and preferably comprises tape tab or mechanical fasteners 401. However, any fastening known in the art will be acceptable. Moreover, the fastening system 40 may include a reinforcement patch below the front waist portion so that the diaper may be checked for soiling without compromising the ability to reuse the fastener. Alternatively, other diaper fastening systems are also possible, including safety pins, buttons, and snaps.

In the preferred embodiment of FIGS. 1–3 absorbent core 342 is a thin, folded, pulpless absorbent core with high SAP efficiency as shown in FIGS. 2 and 3. Of course it should be understood that the underlying structure beneath the topsheet 30 may include, depending on the diaper construction, various combinations of elements. However, in each embodiment, it is contemplated that the absorbent garment will preferably include an absorbent core comprising one or more laminates positioned between the topsheet 30 and backsheet 32. However, in each, at least one of the laminates has a layer preferably containing about 50 to about 95 percent by weight SAP. Thus, the absorbent article will preferably include at least one thin, folded, pulpless absorbent core with high SAP efficiency.

With particular reference to FIGS. 2 and 3, absorbent core 342 is a laminate comprising a central absorbent layer 342a sandwiched between two tissue layers 342b, 342c. More particularly the absorbent laminate 342 comprises an absorbing layer 342a disposed between an inner (also referred to as "upper") tissue layer 342b and an outer (also referred to as "lower") tissue layer 342c.

The folded absorbent laminate 342 has a central channel 360 formed between two side folded areas 370. The central channel 360 extends longitudinally along the central longitudinal axis 60 of the diaper (FIG. 1). The folded structure of the absorbent laminate 342 is formed by folding each of the two marginal sides of the absorbent laminate 342 to form the channel area 360 between the two side folded areas 370.

Without wishing to be bound by any theory of operability, it is believed that the channel 360 and space 371 between two side folded areas 370 provides free volume to temporarily contain multiple doses of liquid such as urine, until the liquid can be absorbed by the SAP material. In the embodiment of FIGS. 1–3, each of the marginal sides are folded once along longitudinal axes 80 and 100. It should be understood however that folding each of the marginal sides once is generally sufficient. It should also be understood that depending on the shape of the cross section of the side folded areas 370, more than two foldings of each marginal side may be necessary.

The side folded areas may extend the whole length of the absorbent core or may be shorter. Also, the width of each side folded area 370 may vary. Generally, it is preferred that the side edges 342d are spaced from one another so that the central channel 360 is open. For the embodiment of FIGS. 1–3 the distance W between side edges 342d is generally from about 0.1% to about 0.9%, preferably from about 0.3% to about 0.7%, and more preferably from about 0.4% to about 0.6% of the total width of the absorbent core in its folded state.

Although in the illustrations of FIGS. 2 and 3 the upper folded surface of the absorbent laminate is depicted as being spaced from the lower surface of the absorbent laminate, in practice, the upper folded surface is in intimate contact with the lower surface thereof. That is, the outer peripheral edges of the absorbent core in the embodiments of FIGS. 2 and 3 have substantially twice the thickness of the central region due to the folds. The channel 360 is formed between opposing side edges 342d of the absorbent laminate.

The absorbent laminate 342 is generally rectangular in shape and preferably does not extend into the ears 302, 303 (FIG. 1) of the absorbent garment, but could be readily modified to do so. The absorbent laminate 342 may optionally be attached to the top layer 301 using a hydrophilic adhesive 346 in an amount of about 2.0 g/sm or less. This is a generally low coverage adhesive application which maintains the liquid permeability of the upper portions 342u of the side folded areas 370. The adhesive is preferably applied using a CONTROLLED FIBERIZATION™ nozzle or DYNAFIBER™ UFD-5. Of course it should be understood that the absorbent core 342 may be attached to the topsheet 30 or backsheet 32 directly or indirectly through intermediate optional laminates or layers.

The absorbent laminate 342 is a thin composite having an overall thickness (FIG. 3) of about 0.5 to 1.1 mm, preferably about 0.7 to about 0.9 mm, and more preferably about 0.8 mm. The basis weight of the absorbent laminate 342 is from about 100 to about 500 g/sm, preferably from about 150 to about 350, and more preferably from about 200 to about 300 g/sm.

In a preferred embodiment, the absorbent layer 342a comprises a layer of fibers that is generally bound to the upper layer 342b. A portion of the SAP material of the absorbent layer 342a is bound to the bottom layer 342c while the remaining unbound SAP is loosely contained in the fibers. The bound SAP is attached to the lower layer 342c by applying an adhesive along a central portion of the lower layer extending along the central longitudinal axis of the lower layer (not shown). The adhesive is preferably a hydrophilic hot melt adhesive having an air/water advancing contact angle of less than about 30°, preferably selected from the group consisting of H2594 and H2561, supplied by AtoFindley, Inc.

The adhesive is utilized at an amount effective to render the central portion of the lower layer 342c substantially liquid impermeable. When H2594 adhesive is used at a basis weight of about 6 g/sm or more, the central portion of the lower tissue 342c is rendered substantially liquid impermeable. Preferably CONTROL COAT or DYNAFIBER™ UFD-17 (center portion of lower layer) and CONTROL WEAVE or DYNAFIBER™ UFD-13 (outer portion of lower layer) spray nozzles are employed to apply the adhesive on the lower layer. The layer of fibers is attached to the upper layer 342b by applying an adhesive on the interior surface of the upper tissue layer at a basis weight of less than about 2 g/sm using CONTROLLED FIBERIZATION or DYNAFIBER™ UFD-5 spray nozzles to maintain the highly liquid porous structure of the upper layer.

Figure 5:
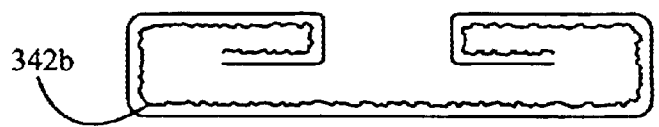
FIGS. 5(a)–5(c) show cross-sections of folded absorbent cores with internal spreading layers.
Figure 5:
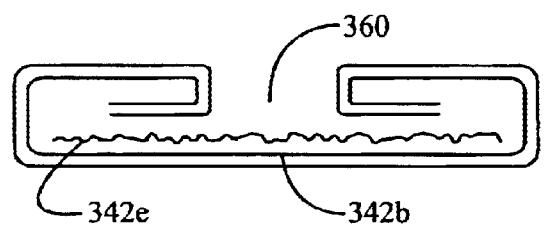
Figure 5:
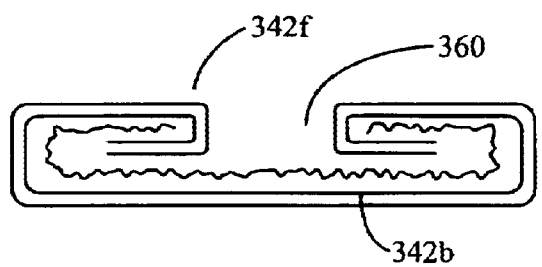

Preferably, the layer of fibers is a tow of cellulose acetate fibers, rayon fibers, lyocell fibers, polyacrylonitrile fibers, surface-modified (hydrophilic) polyester fibers, surface-modified polyolefin/polyester bicomponent fibers, surface-modified polyester/polyester bicomponent fibers, polypropylene fibers, other olefin fibers, cotton fibers, cotton linters or blends thereof., and more preferably a tow of cellulose acetate fibers, rayon fibers, LYOCELL fibers or mixtures thereof. Optionally, a transfer layer (not shown) may be positioned on top of the folded laminate 342. The transfer layer facilitates the transfer of liquid to the folded laminate 342. Also, optionally another spreading layer 342e, such as is shown in FIG. 5, may be placed within the channel area 360. Spreading layer 342e facilitates the transfer of liquid to the internal regions of the folded portions of the absorbent core.

Figure 6:
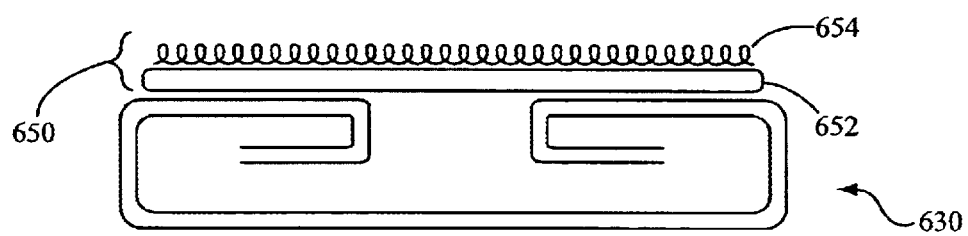
FIG. 6 shows the cross section of a folded absorbent core with an acquisition layer laminate.

Airlaid fluff pulp or synthetic nonwoven are preferred materials, either singly or in combination, for an optional transfer layer 650 (FIG. 6). The optional transfer layer rapidly spreads and transports liquids to the absorbent layer 342. Airlaid pulp basis weights of about 35 to about 100 grams per square meter, and synthetic nonwoven basis weights of about 10 to about 80 grams per square meter are preferred for the optional transfer layer.

In an alternative configuration, the absorbent laminate 342 may optionally be constructed using different combinations of materials for the upper layer 342b and the lower layer 342c. For example, the laminate 342 may comprise an airlaid fluff pulp or a synthetic nonwoven for the upper layer 342b and tissue for the lower layer 342c. Basis weights similar to those above would be preferred for the upper and lower layers of laminate 342.

It will be appreciated that a variety of optional transfer and acquisition layers may be included within the absorbent garment between the topsheet 30 and the backsheet 32. Also, a layer, preferably a tissue layer, may optionally be positioned between a transfer layer (not shown) and the folded absorbent laminate 342 for the purpose of reducing leakage of SAP from the open side edges 342d of the absorbent core. A more detailed discussion of the various optional transfer or acquisition or containing layers can be found in U.S. patent application Ser. No. 09/050,003, which has been incorporated by reference earlier. Each of the laminates and tissue, acquisition or transfer layers are bonded, preferably thermally bonded or adhesively bonded, to adjacent layers. Preferably, hot melt adhesive is used and it is applied to the outer surfaces of the tissue layer of the absorbent laminates and optionally to the surfaces of any tissue, acquisition or distribution layers. Other equivalent laminate configurations are within the scope of the invention, so long as at least one of the absorbent laminates is a folded, thin structure, comprising at least about 50 percent by weight SAP having a SAP efficiency of at least about 70 percent.

For instance an optional upper or transfer layer (not shown) may be positioned on top of the folded laminate 342. The transfer layer is technically not a part of the absorbent core, but rather facilitates the transfer of liquid to the absorbent core. Other laminates and or layers can be used in association with the absorbent core 342. For instance, another absorbent laminate (not shown) may be placed within the channel area 360 of the folded absorbent laminate 342.

Figure 4A:
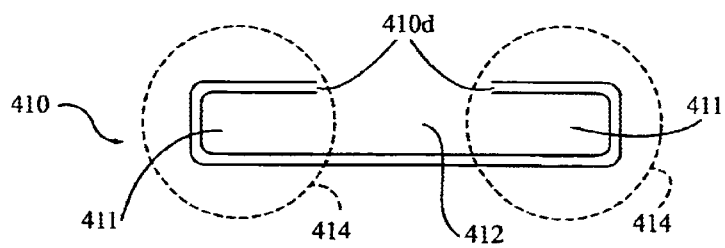
FIGS. 4(a)–4(e) are cross sections of preferred folded absorbent cores.

The side folded areas 370 of the embodiment of FIGS. 1, 2 and 3 have a generally C-shaped cross-section, which has been shown in a state of exaggerated separation in the "C" cross-section to facilitate illustration. It will be appreciated, however, that many different folded structures can be used. Some of preferred folded structures of the absorbent core are shown in FIG. 4. The absorbent cores 410 and 420 of FIGS. 4(a) and 4(b) have generally C-shape sided folded areas 414 and 424, respectively. The absorbent core 410 of FIG. 4(a) is substantially the same as the absorbent core 342 of the embodiment of FIGS. 1–3. The marginal sides of the absorbent core of FIG. 4(a) are each folded once upward to form C-shaped side folded areas 414 and a central channel 412. In the embodiment of FIG. 4(a), side edges 410d of the absorbent core 410 are generally open and spaced by some distance from one another forming a central channel 412 that is generally open at the top.

Figure 4B:
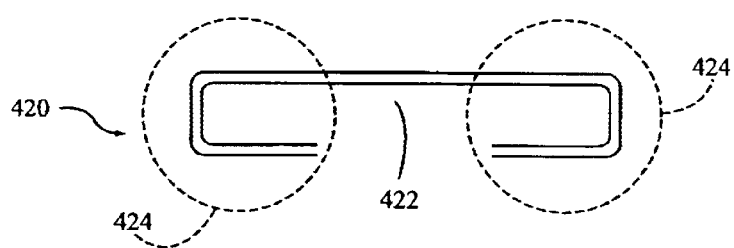
Figure 4C:
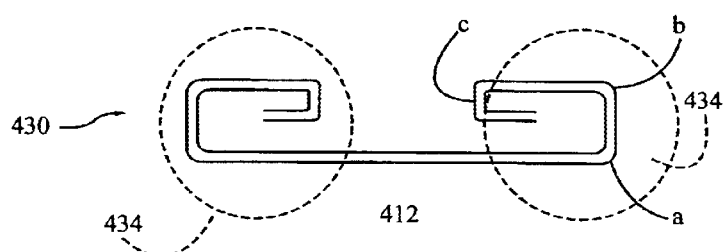

An absorbent core 420 of FIG. 4(b) is substantially a mirror image of the embodiment of FIG. 4(a), with the marginal sides being folded downwardly to form generally C-shaped side folded areas 424 and a central channel 422 therebetween. FIG. 4(c) shows a folded absorbent core having double, longitudinal C-folds. In the embodiment of FIG. 4(c) each marginal side is C-folded twice to form the central channel 412. Again, for purposes of clarity, the C-folds in each of the embodiments of FIGS. 4(a)–(e) are illustrated with a small degree of separation between adjacent surfaces. It will be readily appreciated, however, that the folded layers are in contact with one another when fully constructed. In a most preferred embodiment, as illustrated for example in FIG. 4(c), the absorbent core includes an open channel 412 facing the diaper topsheet. In all of the embodiments, with the exception of FIG. 4(a), the open marginal edges of the absorbent core are positioned either within the folded regions or beneath the body of the absorbent core. These configurations facilitate containment of the SAP.

Figure 4D:
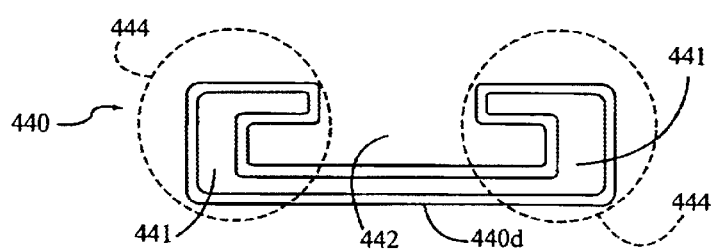
Figure 4E:
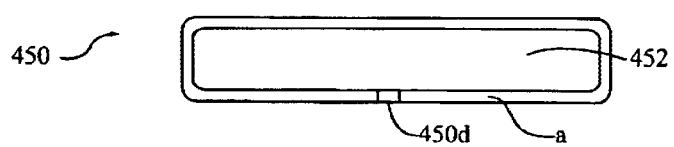

The embodiments of FIGS. 4(d) and 4(e) illustrate alternative embodiments of the absorbent core wherein the side edges 440d and 450d, respectively, come into substantial contact with one another. In the embodiment of FIG. 4(e), the outer layer is rendered porous on top, but impermeable on the bottom through a selective application of adhesives. Other folding configurations for the absorbent core are readily contemplated within the scope of the claimed invention.

The spreading of liquid within the absorbent core can be enhanced by replacing the inner or upper layer in the composite with a material that can function as an internal spreading layer, as in the embodiment of FIG. 5a. Alternatively, as shown in FIG. 5b, a separate internal spreading layer 342e can be cut and placed on top of a portion of the inner layer inside the channel 360. Alternatively, the internal spreading layer can extend substantially the full length of the inner layer as shown in the embodiment of FIG. 5c. Materials suitable for internal spreading layers are low-density absorbent materials such as various airlaid pulp roll good materials, high loft polyester/polypropylene materials, high bulk tissue and absorbent foam materials. Internal spreading layers should provide a low resistance path to bulk liquid flow. Preferably, they provide a low resistance path across substantially their entire area. In addition, if the internal spreading layer replaces the inner layer of the composite, it must also be able to prevent migration of hydrated SAP to the topsheet of the diaper during use.

In the embodiment of FIG. 6, an absorbent, low density acquisition layer 650 is placed on top of the folded absorbent core 630 for improved liquid distribution in the core, particularly when the diaper is worn by active babies that urinate in a standing position. The acquisition layer 650 preferably comprises an absorbent layer 652 and a high-loft nonwoven layer 654. The absorbent layer 652 is preferably made of a high bulk tissue or an airlaid pulp. In one embodiment, the absorbent layer 652 and the high loft nonwoven layer 654 are laminated.

Preferably, for optimal performance, the porosity of the outer layers 342b, 342c of the absorbent composite is modified through material selection and adhesive placement. The inner layer 342b is a high porosity tissue, for example having a porosity of about 40 $ml/cm^2/min.$, for enhanced liquid absorption. Preferably, the lower or outer layer 342c is a high wet strength tissue for enhanced core stability in use, and is rendered less porous, e.g., porosity less than about 5 $ml/cm^2/min.$, as a consequence of the adhesive applications noted previously.

Generally, the porosity of the tissues is reduced by hot melt adhesive application. The extent of the reduction is affected by the amount of the adhesive used, i.e., the adhesive basis weight, and the method employed to apply the adhesive. Generally, tissue porosity is reduced more at a given adhesive basis weight when the adhesive is applied at a higher coverage. The CONTROL COAT™ and DYNAFIBER™ UFD-17 spray nozzles provide high adhesive coverage. The CONTROLLED FIBERIZATION™ and DYNAFIBER™ UFD-5 spray nozzles provide low adhesive coverage. The CONTROL WEAVE™ and DYNAFIBER™ UFD-13 spray nozzles provide medium adhesive coverage. These types of spray nozzles are well known in the art and are provided by the NORDSON Company and ITW Dynatec, noted previously.

Figures 7A, 7B:
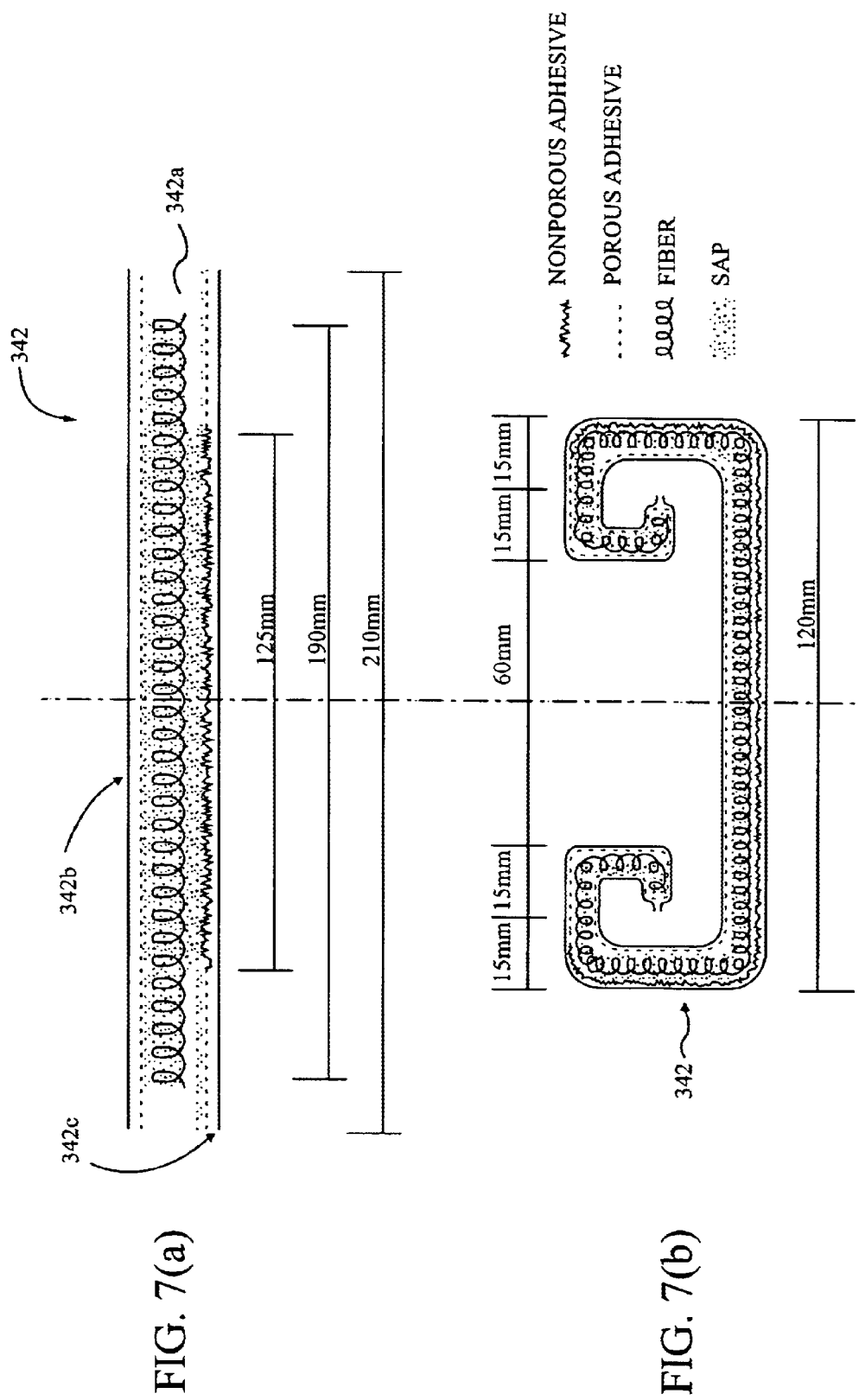
FIG. 7(a) is a schematic representation of an absorbent laminate showing the placement of adhesive between the layers prior to folding.
FIG. 7(b) is a cross-section of the absorbent laminate of FIG. 7(a) after folding.

Attachment of the fiber layer to the upper high porosity tissue layer 342b of the composite is preferably achieved using a spray nozzle that applies less than about 2 g/sm adhesive at low coverage, and preferably about 1.6 g/sm of adhesive, in order to maintain the high liquid porosity of the upper layer (see FIG. 7a).

The lower (also referred to herein as an "outer") tissue layer 342c is attached to the absorbent layer 342a using a generally high coverage of adhesive. Preferably about 2.0–6.0 g/sm, and more preferably about 4.0 g/sm of adhesive, is applied from the spray nozzles. In a particular embodiment shown in FIG. 7, the spray nozzle is used to apply about 2.0–6.0 g/sm of a hydrophilic adhesive down a central portion of the lower tissue extending along a longitudinal axis at a width of about 125 mm, making the central portion of the lower tissue layer highly non-porous and substantially liquid impermeable. Thus, when folded to a width of about 120 mm, the core has a substantially non-porous bottom layer 342c that extends around the outer edges of the core for liquid containment as seen in FIG. 7(b).

Changing the adhesive basis weight of the nozzle-applied adhesive for a given SAP basis weight changes the ratio of bound and unbound SAP in the composite, and affects liquid handling characteristics of the absorbent composite. Generally, bound SAP is attached to the tissue layer and unbound SAP is loosely contained within the fiber layer. On the outer periphery edges of the lower layer 342c, i.e., the outer 30–35 mm edges, about 2.0–5.0 g/sm of adhesive is applied, but at lower adhesive coverage. Consequently, less than about 5.0 g/sm, and more preferably in the particular embodiment of FIG. 7, about 3.0–4.0 g/sm of adhesive was used on the portion of the lower tissue 342c that becomes part of the top section or upper surface of the folded core. The adhesive is applied in moderate coverage to bind SAP and to maintain the porosity of a portion of the lower tissue 342c which, when folded, becomes the upper surface of the outer edge of the folded core, as seen in FIG. 7(b).

The absorbent laminate of the present invention is particularly suitable for narrow crotch diapers and training pants. Narrow crotch training pants either must typically sacrifice absorbent capacity at the narrowed portion as a result of reduced absorbent surface area, or must alternatively provide a thicker absorbent core to compensate for the reduced surface area. As the thickness of the core increases, comfort, fit and wearability decrease. By using the high absorbency thin, folded absorbent laminate according to the various preferred embodiments of the present invention in a narrow crotch absorbent garment, the absorbent capacity through the central crotch area is not sacrificed while comfort, fit and wearability are improved.

Traditional hourglass shaped absorbent cores have pulp/SAP regions extending through the front and rear portions thereof. The ear regions of the absorbent garment thus compensate for the narrow, rectangularly shaped absorbent laminate of the preferred embodiments, which do not extend into the ears of the diaper. This alternative absorbent core design with a narrow crotch can be thought of as a "mixed core." It combines the advantageous features of the absorbent laminate of the preferred embodiments of the present invention with the traditional fluff/SAP absorbent cores.

Figures 12A, 12B, 12C:
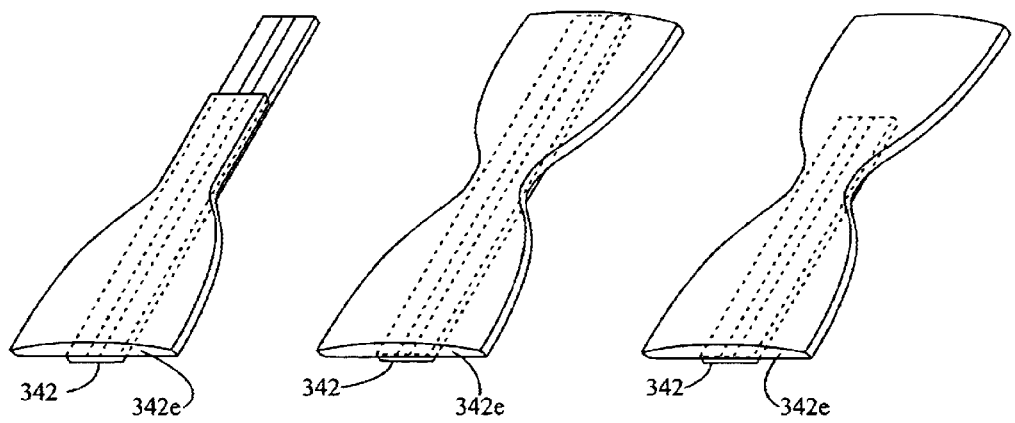
FIGS. 12(a)–12(c) are schematic perspective views of alternative absorbent core embodiments.

For example, as shown in FIGS. 12a–12c, the absorbent core may comprise a variety of alternative embodiments including narrowed crotch regions forming T-shaped or hourglass-shaped cores. More specifically, in the embodiment of FIG. 12a, the mixed core comprises one or more rectangularly shaped, folded laminates 342 of this invention having a high SAP concentration as described above and extending substantially from the front waist region to the rear waist region of the absorbent garment. A T-shaped conventional pulp/SAP partial length absorbent layer 342e may be positioned above the folded absorbent laminate 342 to improve urine acquisition and containment throughout the front half of the absorbent article.

As shown in FIG. 12b, the mixed core may comprise a full length rectangularly shaped folded absorbent laminate 342 including from about 50 to about 95 percent by weight SAP. The mixed core further may include a full length hourglass-shaped conventional pulp/SAP layer 342e positioned above the folded absorbent laminate 342. In the crotch region, the conventional pulp/SAP absorbent layer is narrowed for improved comfort and fit. Finally, as shown in FIG. 12c, the mixed core, according to the preferred embodiments, may include a partial length folded absorbent laminate 342 comprising about 50 to about 95 percent by weight SAP. A full length, hourglass-shaped conventional pulp/SAP layer 342e may be positioned above the folded absorbent laminate 342. In the crotch region, the conventional pulp/SAP layer is narrowed for improved comfort and fit. Although only one absorbent laminate 342 is depicted in FIGS. 12a–12c, additional absorbent laminates, each of which contains a central absorbent (or central absorbing), layer comprising the amounts of SAP set forth above, may be positioned above, below or inside the channel 360 or above the conventional pulp/SAP absorbent layer 342e. Absorbent laminates in accordance with the present invention, used in narrow crotch absorbent cores, should preferably have a total basis weight in the range of from about 150 to about 600 g/sm.

Total basis weights of the absorbent core 342, including SAP, tissue and additives, are about 150 to about 600 grams per square meters, most preferably about 200 to about 300 g/sm. The fibrous and/or particular additives, can be used in the amounts discussed above with the laminates 342. Such additives maintain high SAP efficiency at high SAP concentrations. For example, it has been unexpectedly discovered that the SAP efficiency improves to about 85 percent in a 250 grams per square meter composite comprised of 80 percent SAP, 10 percent cellulose acetate, and 10 percent fluff pulp, whereas in a composite comprised of 80 percent SAP and 20 percent fluff pulp, SAP efficiency is about 70 percent.

Optionally, from about 1 to about 10 percent, preferably about 5 percent, by weight of thermally bondable synthetic fibers can be added to the absorbent layer of the central laminate 340 to impart additional wet strength to the laminate. This will improve the stability of the absorbent core during use of the diaper. The preferred synthetic fibers are polyolefin/polyester fibers and polyester/polyester bicomponent fibers.

While, as discussed above, the present invention is premised in part on the unexpected discovery that certain fibrous and particulate additives maintain high SAP efficiencies when the SAP concentration is in the range of about 50 to about 95 percent by weight, thin, fluff/SAP cores that include greater than about 50 percent SAP require additional structural or design measures to contain the SAP in the core and provide adequate wet strength for core stability in manufacture and use. One solution is the careful selection and application of adhesives for controlling the porosity of the inner layer 342b and outer layers 342c of the absorbent laminate. Another solution resides in the unexpected discovery that a high SAP concentration absorbent layer 342a may be hydrogen bonded to the fibrous or particulate additives and/or to the inner or outer layers of the absorbent laminate. When a highly concentrated SAP-containing absorbent layer is hydrogen bonded to the fibrous or particulate additive and/or the inner and outer layers, the SAP efficiency is not impaired, wet strength increases, and the inner and outer layers add stability to the core during manufacture. Hydrogen bonding is described in U.S. Pat. No. 5,609,727 which is incorporated herein by reference for all purposes and in a manner consistent herewith. Hydrogen bonding can be used when the SAP-containing absorbent layer includes fibrous additives. Briefly, the fibers may be sprayed with water to promote hydrogen bonding in a dry formed composite or the fibers may be treated with a plasticizer, such as triacetin, in either a dry or wet process. The triacetin promotes fiber to fiber bonding and can improve wet and dry integrity of the composite. The water and the triacetin treatments are useful in adjusting the density of the composite.

Prior art roll good SAP composites containing 50 to 95 percent SAP are often too weak for processing on a diaper machine, have inadequate wet strength for in-use core stability, and the SAP is not secured within the composite. Those roll goods that have adequate strength tend to have low SAP efficiency, because they restrict swelling of the SAP within the composite. Attempts to bond the SAP within the composite invariably reduce the absorbency and efficiency of the composite. The absorbent cores of the preferred embodiments solve the prior art problems of maintaining adequate levels of dry tensile strength, core stability in use, and SAP containment.

When the inner and outer layers are tissue layers and are hydrogen bonded using water or other bonding agents to bond to the absorbent layer, unexpectedly good "core utilization" is realized. "Core utilization" is measure of the percentage of the total capacity of a core that can be absorbed in a whole core demand absorbency test.

The preferred fiber-containing absorbent core laminates have an optimum density for SAP efficiency and core utilization. This is believed to occur because, generally, SAP efficiency decreases and core utilization increases as the core density increases. Thus, a compromise is usually made. For an absorbent laminate including an absorbent layer comprising about 20 percent cellulose acetate and 80 percent SAP and having a basis weight of from about 200 to about 300 g/sm, the optimum density range for the absorbent layer 342a is preferably from about 0.15–0.35 g/cc, and more preferably about 0.25 g/cc.

Figure 8:
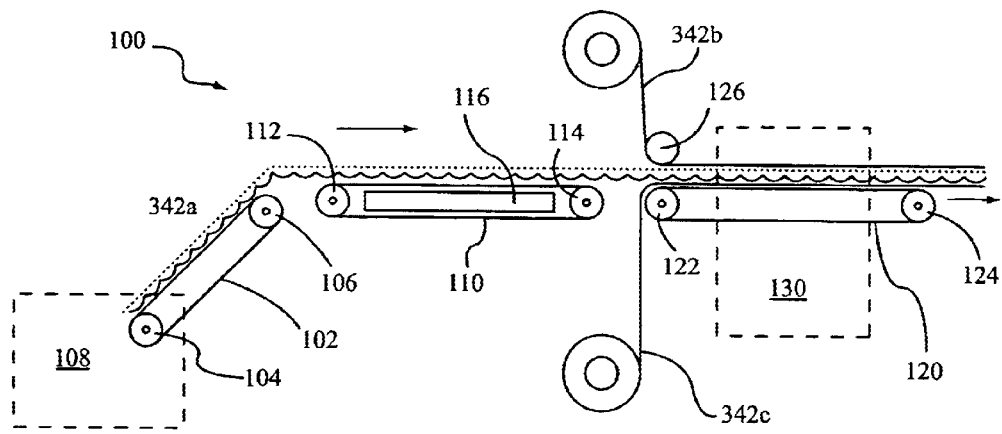
FIG. 8 is a schematic illustration of one method of manufacturing the laminate absorbent core of the preferred embodiments.
Figure 9:
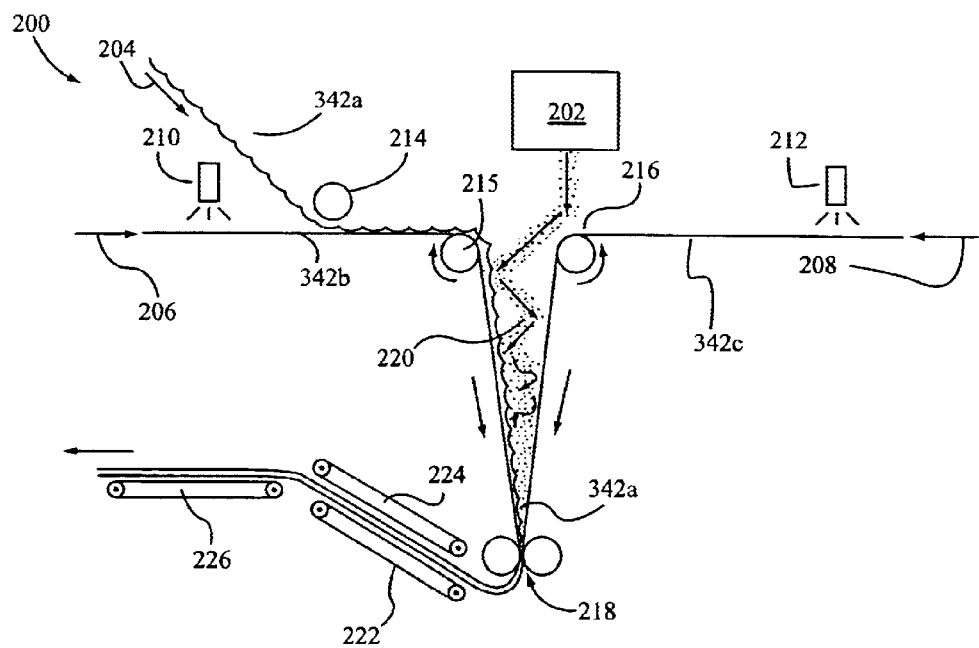
FIG. 9 is a schematic illustration of another method of manufacturing the laminate absorbent core of the preferred embodiments.
Figure 11:
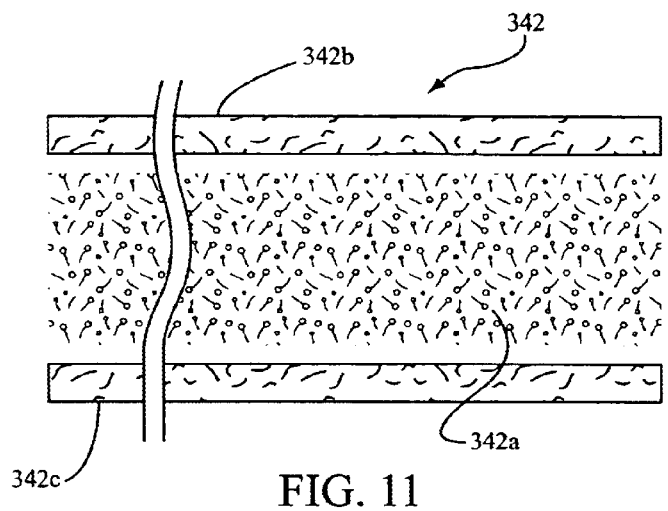
FIG. 11 is a cross-section of one of the laminates of the absorbent core of the preferred embodiments.

The foregoing absorbent laminates of the preferred embodiments may be made using both wet and dry processes, described below. With reference to FIGS. 8–9, examples of manufacturing processes for producing the absorbent laminates of FIGS. 7 and 11 according to wet and dry processes, respectively, are schematically illustrated. FIG. 11 shows an absorbent laminate of the present invention in its unfolded stage including a central absorbent layer 342a comprising SAP fibrous and/or particulate additives. The upper and lower layers 342b and 342c are preferably tissue, airlaid fluff pulp or synthetic nonwoven materials.

The fiber/particulate and SAP forming the central absorbent layer 342a of the absorbent laminate 342 of FIG. 11 can be made using conventional wet processes such as, for example, conventional wet-laid nonwoven processes utilizing Valmet's high dilution Deltaformer or Rotoformer, an aqueous foam-based forming process, or a process of coating a porous substrate with a solvent/water-based suspension of the stabilization additives (fiber and/or particulate) and SAP. An example of one such wet process is carried out with a machine available from Neue Bruderhaus AG schematically illustrated in FIG. 8. There, the manufacturing line 100 for forming a laminate 342 comprises a first endless conveying system (or "conveyor") 102, e.g., felt or wire mesh, extending between rollers 104, 106. The conveyor 102 is inclined, with its lower end submersed within an aqueous suspension or slurry 108 of fibrous/particulate additives ("stabilization additives") and SAP. The conveyor 102, depending on the angle of incline and the static friction of the felt or wire mesh, entrains a predetermined amount of slurry from the bath 108. The composite slurry of SAP and the stabilization additives is delivered to a second conveyor 110.

The second conveyor 110 likewise includes rollers 112, 114, between which extends a mesh wire or felt. A suction dewatering device 116 is positioned within conveyor 110. Water is removed from the fibrous/particulate additive and SAP composite slurry 342a, upon which the composite slurry is delivered to a third conveyor 120. The third conveyor includes rollers 122, 124, between which extends a mesh wire. Upper and lower layers 342b, 342c of the absorbent laminate 342 are formed as roll goods positioned above and below the central layer 342a. The upper and lower layers 342b, 342c may comprise tissue, airlaid fluff pulp or synthetic nonwoven. A nip roller 126 presses the upper layer 342b into intimate encasement with the upper surface of an absorbent layer 342a. Likewise, a roller 122 presses the lower layer 342c into intimate engagement with the lower surface of the absorbent layer 342a.

Finally, a drying oven 130 is positioned around the third conveyor. The drying oven heats the fiber absorbent core laminate 342, removing excessive water, and causing the adjacent layers to intimately bond together, either by thermal bonds or hydrogen bonds. If the upper or lower layer is a synthetic nonwoven, or contains thermally bondable fibers, it can bond to the thermally bondable fibers included in the wet-laid middle layer 342a for added wet strength. Additional bonding strength can be imparted by hot calendaring or thermal point bonding.

FIG. 9 illustrates a preferred dry forming method and apparatus for making an absorbent laminate of the present invention. The dry forming process typically has lower conversion costs than the wet process, since the equipment used in a dry process is typically less complex and can run at higher line speeds. Further, the dry forming process could be adapted for use on individual diaper machines rather than forming the absorbent composite laminate off line, which is then prepared as a roll good as in the wet process. Alternatively, wet processes may be employed on or off line.

One of the challenges in a dry forming process is achieving homogeneous mixing of SAP with other components, i.e., fibrous or particulate additives, of the absorbent layer 342a of the laminate. With the proper geometry of the web path, substantial homogeneous mixing of SAP and the other components can be realized. The preferred dry forming machine 200 of FIG. 9 includes a SAP bin 202, a fiber feed path 204, an upper layer feed path 206 and a lower layer feed path 208. Hot melt adhesive spray applicators 210, 212 apply adhesive to the inner surfaces of the upper and lower layers 342b, 342c, respectively. Hydrophilic hot melt adhesives are effective processing aids but not critical in the construction of the dry laminates if hydrogen bonding is used. A typical application level of hot melt adhesive is about 1–10 g/sm per layer.

A roller 214 intimately encases the fibrous additive 342a from the feed path 204 with the upper layer 342b. SAP is vertically dropped from a SAP bin 202 to a point above roller 216. A region of high turbulence 220 is generated between the upper layer 342b and the lower layer 342c of the laminate just before a nip point (or "nip") 218 that stabilizes the structure. The high turbulence or mixing chamber 220 is designed so that the angle and high speed of the moving web causes the SAP fibrous or particular additives stream to be deflected downward toward the upper layer 342b, to which the fibrous additive component is attached. The SAP bounces back and forth between the upper and lower layers 342b, 342c, effectively and evenly distributing the SAP within the fibrous component. SAP lost at the edges of the 2 to 4 meter wide web can be collected and recycled back into the process. When the laminate 342 is compressed at the nip 218, the SAP is uniformly mixed and effectively locked within the structure.

If, for improved absorbency, hydrogen bonding is desired in the dry forming process, after the absorbent layer is formed, the upper and lower layers 342b, 342c may be lightly wetted between the endless conveyors 222, 224, and then dried at the drying conveyor 226 incorporating either an IR oven or an air dryer. When making a cellulose acetate-SAP-tissue laminate, triacetin or any other compounds suitable for fiber to fiber bonding can be dispersed in the water of the wetting section corresponding to conveyors 222, 224 to provide additional bonding within the structure. When water with a hydrogen bonding-inducing compound is used, the consumption of hot melt adhesive may be reduced significantly.

Figure 10:
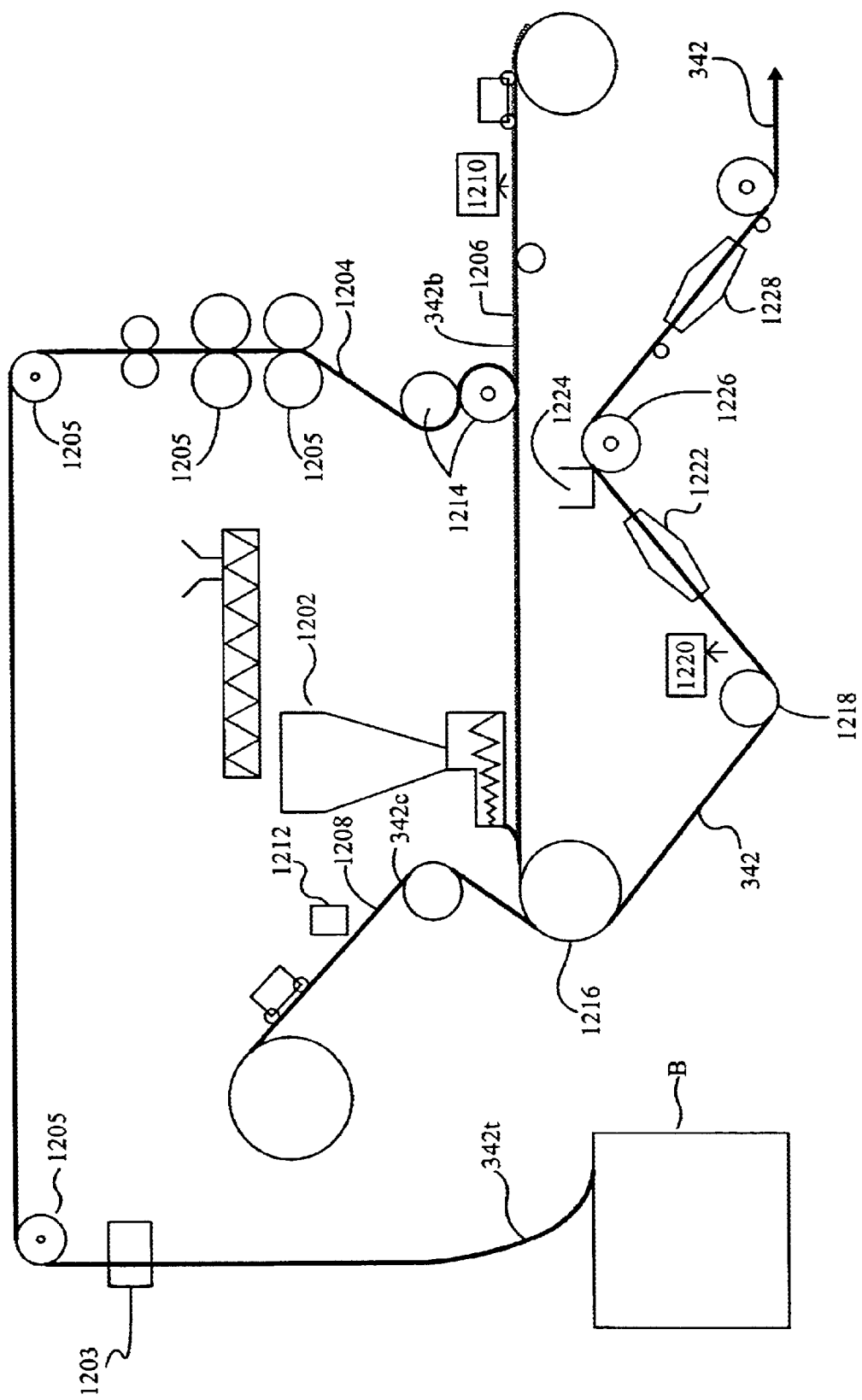
FIG. 10 is a schematic illustration of yet another method of manufacturing the laminate absorbent core of the preferred embodiments.

FIG. 10 illustrates a preferred dry formed core (DFC) method for making a thin, folded, pulpless absorbent laminate such as, for example, absorbent laminate 342 of FIGS. 2 and 3. The dry forming machine of FIG. 10 includes a SAP bin 1202, a fiber feed path 1204 carrying a tow of fibrous material 342t from a bale B, an upper layer feed path 1206 carrying an upper layer 342b, and a lower layer feed path 1208 carrying a lower layer 342c. A suitable fibrous material is cellulose acetate, but other materials may be used. Various rolls 1205 are employed in the fiber feed path 1204 to move the fibrous tow 342t along the fiber feed path 1204.

The porosity of the outer layers 342b and 342c of the absorbent core laminate is modified through material selection and adhesive placement, as discussed previously. The upper layer 342b is a high porosity tissue for enhanced liquid absorption. The lower layer 342c is a high wet strength tissue for enhanced core stability in use. Hot-melt, adhesive spray applicators 1210, 1212 apply the adhesive to the inner surfaces of the upper and lower layers 342b, 342c. The adhesive applicator 1210 is preferably a spray nozzle that applies less than about 2 g/sm, preferably about 1.6 g/sm of a hydrophilic adhesive at low coverage to the inside surface of the upper layer 342b in order to maintain the high liquid porosity of the upper layer 342b.

The adhesive applicator 1212, which is preferably a spray nozzle, applies a hydrophilic adhesive at high coverage on top of a central band-like region along the central longitudinal axis of the lower tissue 342c at an application width of about 125 mm. Of course, the width of the central band-like region may vary depending upon the overall size of the diaper and the folded structure type of the absorbent core. The hydrophilic adhesive is applied at an amount of greater than about 2–8 g/sm, preferably greater than about 6 g/sm to render the lower layer 342c substantially liquid impermeable. Outside of the 125 mm wide central band, preferably less than about 6 g/sm (i.e., medium coverage) of adhesive is applied using a spray nozzle to maintain the porosity of the marginal sides of the lower tissue which, when folded, form the upper, outer peripheral surface of the folded absorbent core.

The fibrous component of the absorbent layer 342a is most preferably a crimped tow of cellulose acetate or polyester. Alternatively, the fibrous component of the absorbent layer 342a may be a low-density roll good made in a separate process. Still further yet, the fibrous component could also be a meltblown or carded web formed on-line.

Alternatively, an absorbent laminate may be made directly on a diaper converting machine. In such an embodiment, the laminate is formed using the dry process wherein tissue layers 342b, 342c are wider than the fiber/SAP layer in order to reduce SAP losses along the edges of the absorbent laminate. The edges 342b, 342c of the laminate may optionally be adhesively attached to completely envelop and contain the fiber/SAP layer.

Feed rolls 1214, comprising two rollers, apply the fibrous tow to the upper layer 342c. Downstream of the feed roll assembly 1214, the SAP material is vertically fed from the SAP bin 1202 onto the tow 342t prior to reaching a vacuum roller 1216. The SAP is forced within the voids of the fibrous additive tow 342t as the laminate 342 consisting of an upper layer 342b, a fibrous tow 342t, SAP, and a lower layer 342c is passing over the vacuum roller 1216. At this point, the SAP is bonded to the lower layer 342c and loosely contained within the fiber layer. The laminate 342 is then stabilized using a nip roller 1218. Optionally, SAP lost at the edges of the fibrous web is collected and recycled back into the process (not shown). When the laminate 342 is compressed at the tension roller 1218, the SAP material is uniformly mixed and effectively locked within the porous, web structure of the fibrous tow 342t. It is believed that a portion of the individual SAP particles are typically not bonded to the fibrous additive or the outer layers, but are rather preferably locked within the absorbent layer 342a due to the pore size of the fibrous additive.

Downstream of the tension roller 1218, an optional adhesive applicator 1220 can be employed to stabilize the first C-fold. The laminate is then directed through a first folding apparatus 1222, whereby a first C-fold is formed. A second adhesive application is provided by adhesive applicator 1224 to the surface of the laminate, i.e., the upper layer 342b. The laminate is then directed over tension roller 1226 and through second folding apparatus 1228 to impart a second C-fold. The second adhesive application stabilizes the folded core. The folding techniques employed in the preferred embodiments to obtain the C-folded laminate are well known to those skilled in the art. The folded laminate 342 (as illustrated in cross section in FIG. 7b) is then fed into a diaper converting machine downstream of the second folding apparatus 1228.

The adhesive applications are preferably applied to the upper and lower layers resulting in the dimensions illustrated in FIG. 7a. Then, the core may be C-folded twice to produce an absorbent core 342 having the dimensions similar to those illustrated in FIG. 7b.

Additionally, the SAP particle diameters of the preferred embodiments are preferably less than about 600 μm. It has been discovered that particle sizes substantially greater than about 600 μm cause the laminate 342 to feel gritty to the touch.

As will be appreciated, several permutations and combinations of the thin, folded, pulpless absorbent laminates are possible. Without intending to limit the claimed invention or equivalents thereof, some of the preferred exemplary absorbent laminates for use in an absorbent core of an absorbent garment include those described in the following examples.

EXAMPLES

Examples 1–6

The following examples in Table 1 below may be used as absorbent core laminates in disposable absorbent articles within the scope of the preferred embodiments:

TABLE 1

EXEMPLARY THIN, FOLDED, PULPLESS ABSORBENT CORE LAMINATES

| Example | Laminate Basis Weight, Not including adhesive (g/sm) | Absorbent Laminate | | |
|---|---|---|---|---|
| | | Upper Layer | Central Layer | Lower Layer |
| 1 | 202 g/sm | Polypropylene nonwoven 20 g/sm | 75% SAP; 20% Cellulose Acetate 160 g/sm | Tissue 22 g/sm |
| 2 | 238 g/sm | Tissue 16 g/sm | 80% SAP; 20% Cellulose Acetate 200 g/sm | Tissue 22 g/sm |
| 3 | 267 g/sm | Latex-bonded 65 g/sm | 90% SAP; 10% Cellulose Acetate 180 g/sm | Tissue 22 g/sm |
| 4 | 288 g/sm | Tissue 16 g/sm | 70% SAP; 20% Cellulose Acetate; 10% Bico 250 g/sm | Tissue 22 g/sm |
| 5 | 351 g/sm | Tissue 16 g/sm | 60% SAP; 20% Cellulose Acetate; 15% Polyester; 5% BICO 300 g/sm | Tissue 35 g/sm |
| 6 | 242 g/sm | Tissue 35 g/sm | 85% SAP; 10% Cellulose Acetate; 5% Corn Starch 190 g/sm | Polypropylene nonwoven 17 g/sm |

The SAP in examples 1 through 6 are preferably commercially available superabsorbent polymers having a high FVAUL, for instance, an FVAUL value greater than about 50 cm$^3$. Commercially available SAP which can be used in the preferred embodiments of the invention includes IM7200 and IM7700, manufactured by BASF of Portsmouth, Va. Either of these superabsorbent polymers may be used in any of the foregoing examples 1–6 to achieve the desired absorbency characteristics. FVAUL is a measure of the gel blocking characteristics of the superabsorbent polymer and laminates containing superabsorbent polymer.

FVAUL is a proprietary test method of Paragon Trade Brands, the assignee of the present invention. The FVAUL test method comprises a method for measuring the increase in volume or swelling of a partially hydrated sample of SAP using multiple doses of liquid. Units of FVAUL can be expressed as cc/60 ml, when 60 ml (3 doses of liquid at 20 ml/dose) are used in a standard test protocol. FVAUL is a representative measure of the gel blocking of the SAP used in the laminate.

The apparatus for determining FVAUL comprises a cylindrical, open top sample holder for receiving a sample of the SAP. The inside radius of the sample holder is about 1 inch. A cylindrical telescoping tube having a screen secured at its bottom surface is placed on the sample contained in the sample holder. The cylindrical tube further comprises a means for supporting a cylindrical weight with an open center in place to apply a uniform pressure of 0.5 psi to the sample, while allowing the sample to expand freely in a vertical direction. As liquid is poured into the cylindrical tube, it is evenly distributed through the screen on the top surface of the sample inside the holder, and the partially hydrated SAP sample swells. An LVDT device is positioned above the cylindrical tube such that the core of the LVDT rests on the screen of the cylindrical tube. The thickness of the sample defines the reference volume, which is set to 0. The LVDT measures the increase in thickness of the sample as it swells. Data collected from the LVDT are fed into a computer to record the increase in volume of the partially hydrated sample over a period of, typically, about 60 min. In a standard test protocol, about 3 g. of SAP and three substantially 20 ml doses of a 0.9 wt. % saline test solution are used. The doses are typically spaced at about 20 min. intervals.

Figure 13:
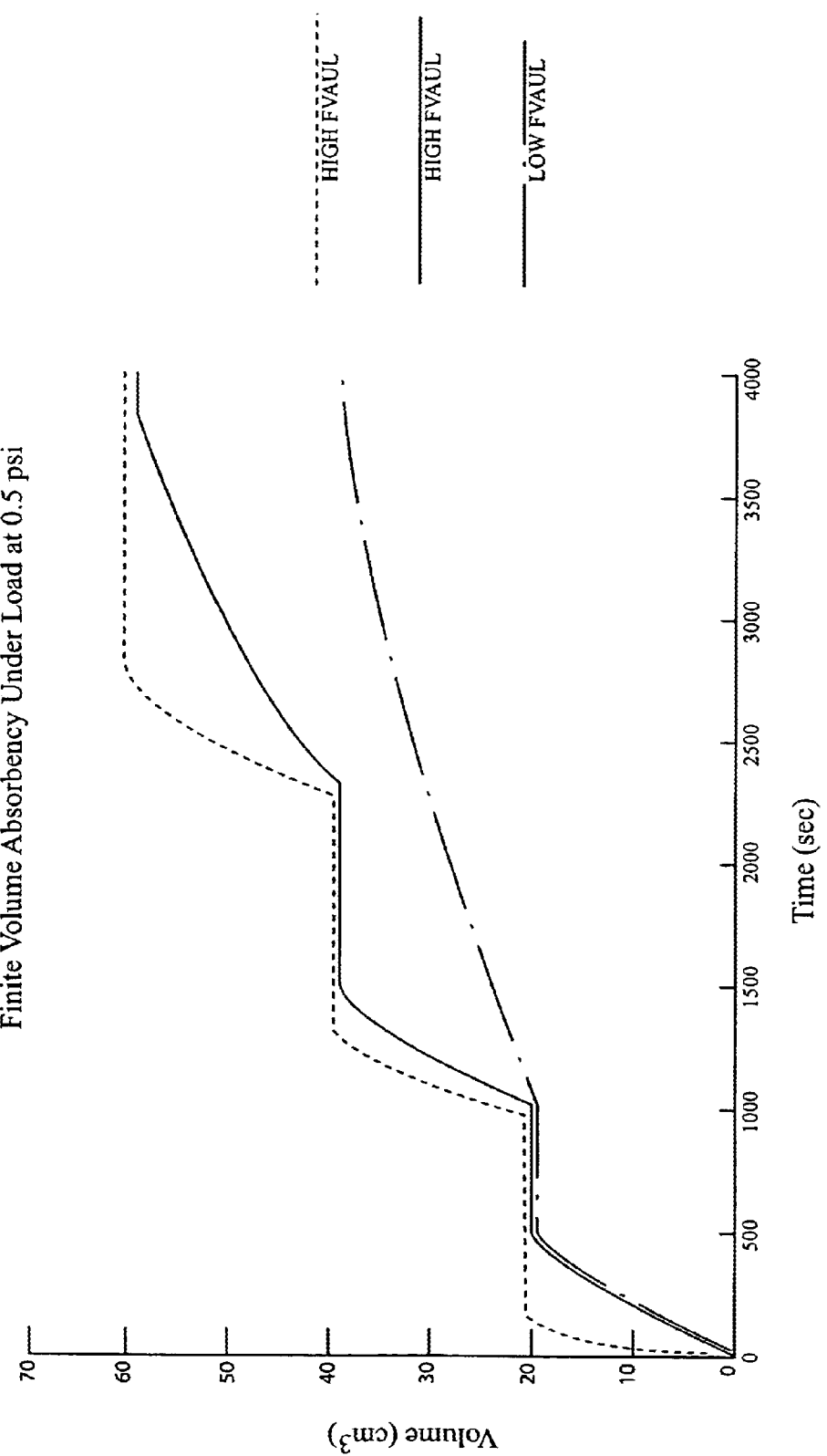
FIG. 13 illustrates finite volume absorbency under load (FVAUL) at 0.5 psi for three SAPs.

In FIG. 13, results obtained in the FVAUL test for two high-FVAUL SAP's, preferred for the absorbent laminate (e.g., FVAUL greater than about 50 cc/60 ml), are compared to those obtained for a low-FVAUL SAP.

The absorbent laminate comprising SAP and cellulose acetate in examples 1–6 are preferably made according to the preferred DFC method of FIG. 10 described earlier. The absorbent of examples 1–6 realize SAP efficiency from about 50 to about 95 percent, and more preferably greater than about 70 percent. The efficiency of the SAP in the absorbent laminate is greater than the efficiency of the SAP in a conventional pulp/SAP absorbent core at comparable SAP concentrations.

SAP efficiency is a measure of the effectiveness of SAP. SAP efficiency is the ratio, expressed as a percentage, of the actual SAP absorbency under load (AUL) expressed as grams of saline absorbed per gram of SAP in the laminate, and the maximum SAP AUL obtained under ideal conditions of low basis weight where gel blocking does not occur. The AUL of SAP in the composite is expressed as grams/grams of SAP in the composite and is determined by measuring the AUL of the composite with and without SAP.

Examples 1–6 exhibit a marked increase in core efficiency as compared with conventional high concentration SAP/pulp absorbent cores, which typically exhibit core efficiencies of about 70 percent. The following chart summarizes pulp/SAP cores of various compositions. AUL defines the uptake of liquid of a specimen while a load is applied to the specimen. AUL is a well known test and is described in U.S. Pat. No. 5,147,343, which is incorporated herein by reference for all purposes and to the extent that is consistent with the present application.

| ABSORBENT CORE LAMINATE | AUL* (g/g) of SAP | SAP Efficiency (%) |
|---|---|---|
| SAP Only 40 g/sm | 34.4 | Reference (100%) |
| SAP Only 80 g/sm | 24.8 | 72% |
| SAP Only 160 g/sm | 15.1 | 44% |
| SAP Only 320 g/sm | 10.6 | 31% |
| Pulp/SAP Mixture 20% Pulp/80% SAP 400 g/sm total | — | 46–64% |
| Absorbent Laminate 20% Cellulose Acetate/80%/SAP 200 g/sm total | — | 72–83% |

*AUL determined in a sample holder having an inside diameter of 2 inches. AUL is the mass of a 0.9 wt. % saline test solution absorbed by the sample after 30 min. under a restraining pressure of 0.5 psi.

Porosity/SAP Bonding Examples

Examples A1–C8 of Tables 2 and 3 below show the effects of adhesive type and pattern on porosity and superabsorbent bonding, respectively.

"Porosity" is defined as the time it takes for 100 ml of 0.9% saline solution to penetrate through a circular portion of the absorbent layer being 2 inches in diameter and is generally expressed in units of ml/cm$^2$/min or seconds. "Superabsorbent bonding" is the amount of SAP that is bonded to the adhesively coated tissue layer in the laminate.

Porosity results in Table 2 are reported in seconds, though porosity may also be expressed in units of ml/cm$^2$/min. Ten (10) samples were measured for each condition.

H2561, a hydrophilic construction adhesive using a resin ester tackifier and H2594, a hydrophilic construction adhesive using a hydrocarbon tackifier, were compared to a control hydrophobic construction adhesive. The control hydrophobic adhesive is typical of the hot melt type adhesives commercially available for diaper constructions and well known to those skilled in the art. Spiral Spray (SS) also referred above as CONTROLLED FIBERIZATION™, CONTROL COAT™ (CC) and CONTROL WEAVE™ (CW) spray methods were included.

For "SAP bonding," a 4 gm/m$^2$ adhesive add-on was used. Adhesive was applied to the high wet strength (HWS) tissue and combined to a release paper. "Superabsorbent bonding" was measured by allowing superabsorbent to touch the adhesive coated HWS tissue, shaking the laminate, and measuring the mass of superabsorbent bonded to the tissue. The laminate size was 0.01 m$^2$. Ten (10) samples were measured for each condition.

For the "porosity" study, the three methods of adhesive application were tested at 4 and 6 gm/m$^2$ adhesive add-ons. The test samples consist of a HWS and porous tissue adhesively laminated using various adhesive spray nozzles and adhesive basis weights. The test samples were made by spraying adhesive on a HWS tissue. For ease of handling, a porous tissue was then placed on HWS tissue to create a lamination.

Figure 14:
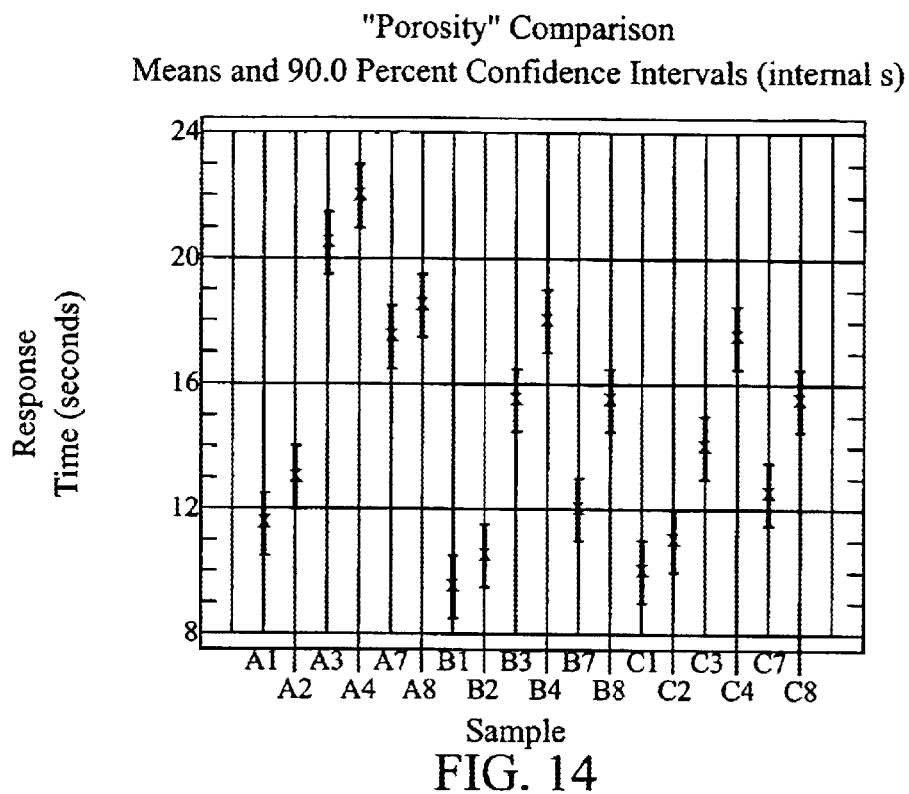
FIG. 14 shows porosity results for various adhesives and adhesive application patterns.
Figure 15:
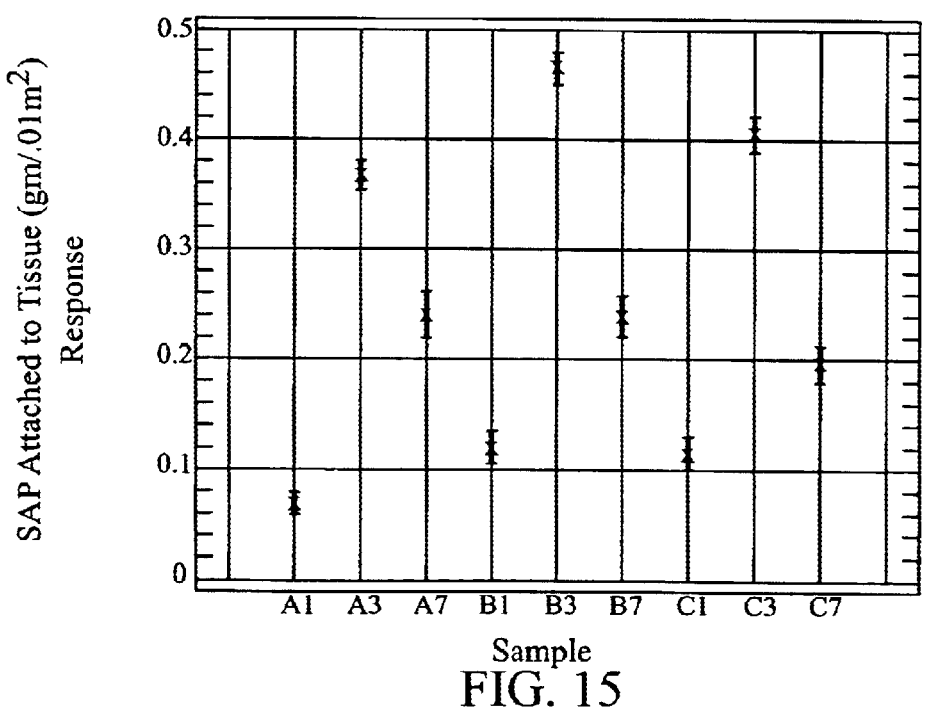
FIG. 15 shows superabsorbent bonding results for various adhesives and adhesive application patterns.

FIGS. 14 and 15 summarize the "porosity" and "superabsorbent bonding" results of the absorbent core laminates of Tables 2 and 3. The data in FIGS. 14 and 15 and Tables 2 and 3 demonstrate how selective application of adhesive can be used to affect the porosity of the outer layers of the laminate and the attachment of SAP and the bonding of SAP within the laminate. Overall, both hydrophilic adhesives, H2561 and H2594, show significantly improved porosity and good superabsorbent bonding compared to the hydrophobic control adhesive. Moreover, the adhesive pattern can be tailored for each application to improve performance.

Specifically, for the upper layer where maximizing porosity is critical, either Spiral Spray or Control Weave (with low air pressure), to allow bigger fibers with more open area are preferred. Also, hydrophilic adhesives such as H2561 and H2594 generate a significant performance improvement. For the lower layer where maximizing superabsorbent bonding is critical, either Control Coat or Control Weave (with higher air pressure to allow smaller fibers with higher fiber coverage) are preferred.

TABLE 2

Adhesive/Application Pattern Comparison Fluid Penetration - Porosity
"HWS" Tissue to "Porous" 1 Tissue - For "Porosity" Testing*

| Examples | Adhesive | Application | Add-On (gm/m$^2$) | 1 | 2 | 3 | 4 | 5 | 6 | 7 | 8 | 9 | 10 | AVE | STD |
|---|---|---|---|---|---|---|---|---|---|---|---|---|---|---|---|
| A1 | phobic | Spiral | 4 | 11 | 10 | 8 | 14 | 12 | 11 | 13 | 12 | 15 | 14 | 12.00 | 2.11 |
| A2 | phobic | Spiral | 6 | 15 | 13 | 14 | 12 | 13 | 13 | 12 | 13 | 13 | 15 | 13.30 | 1.06 |
| A3 | phobic | Control Coat | 4 | 19 | 20 | 21 | 21 | 18 | 21 | 23 | 18 | 21 | 21 | 20.30 | 1.57 |
| A4 | phobic | Control Coat | 6 | 20 | 23 | 21 | 25 | 21 | 24 | 25 | 21 | 21 | 19 | 22.00 | 2.00 |
| A5 | phobic | Control Weave | 1 | 13 | 9 | 10 | 15 | 9 | 11 | 8 | 18 | 10 | 12 | 11.30 | 2.67 |
| A6 | phobic | Control Weave | 2 | 11 | 12 | 13 | 15 | 13 | 13 | 11 | 18 | 11 | 11 | 12.80 | 1.78 |
| A7 | phobic | Control Weave | 4 | 17 | 18 | 18 | 18 | 19 | 16 | 18 | 17 | 16 | 18 | 17.50 | 0.97 |
| A8 | phobic | Control Weave | 6 | 18 | 21 | 17 | 19 | 18 | 18 | 23 | 18 | 15 | 18 | 18.50 | 2.17 |
| B1 | H2561 | Spiral | 4 | 8 | 9 | 10 | 11 | 11 | 7 | 11 | 11 | 9 | 7 | 9.40 | 1.65 |
| B2 | H2561 | Spiral | 6 | 10 | 12 | 9 | 9 | 12 | 13 | 11 | 9 | 9 | 9 | 10.30 | 1.57 |
| B3 | H2561 | Control Coat | 4 | 15 | 14 | 16 | 15 | 15 | 6 | 16 | 15 | 14 | 16 | 15.20 | 0.79 |
| B4 | H2561 | Control Coat | 6 | 16 | 17 | 20 | 16 | 20 | 19 | 20 | 18 | 18 | 18 | 18.20 | 1.55 |
| B5 | H2561 | Control Weave | 1 | 10 | 9 | 8 | 10 | 10 | 9 | 10 | 9 | 9 | 10 | 9.40 | 0.70 |
| B6 | H2561 | Control Weave | 2 | 10 | 9 | 9 | 12 | 10 | 9 | 10 | 12 | 12 | 9 | 10.20 | 1.32 |
| B7 | H2561 | Control Weave | 4 | 13 | 12 | 11 | 13 | 12 | 10 | 13 | 11 | 12 | 12 | 11.90 | 0.99 |
| B8 | H2561 | Control Weave | 6 | 13 | 14 | 15 | 15 | 17 | 16 | 15 | 12 | 18 | 17 | 15.20 | 1.87 |
| C1 | H2594 | Spiral | 4 | 10 | 11 | 9 | 9 | 8 | 11 | 9 | 11 | 9 | 10 | 9.70 | 1.06 |
| C2 | H2594 | Spiral | 6 | 11 | 13 | 9 | 10 | 9 | 10 | 13 | 11 | 9 | 9 | 10.40 | 1.58 |
| C3 | H2594 | Control Coat | 4 | 15 | 18 | 14 | 13 | 13 | 17 | 11 | 13 | 14 | 14 | 14.20 | 2.04 |
| C4 | H2594 | Control Coat | 6 | 17 | 18 | 20 | 16 | 15 | 19 | 20 | 16 | 18 | 18 | 17.50 | 1.78 |
| C5 | H2594 | Control Weave | 1 | 10 | 9 | 9 | 9 | 11 | 10 | 10 | 9 | 11 | 11 | 9.90 | 0.88 |
| C6 | H2594 | Control Weave | 2 | 11 | 10 | 9 | 10 | 9 | 12 | 11 | 11 | 10 | 11 | 10.40 | 0.97 |
| C7 | H2594 | Control Weave | 4 | 13 | 12 | 11 | 14 | 15 | 13 | 17 | 13 | 9 | 12 | 12.90 | 2.18 |
| C8 | H2594 | Control Weave | 6 | 15 | 15 | 19 | 11 | 13 | 16 | 18 | 15 | 15 | 15 | 16.20 | 2.25 |

*3 patterns each application - 120 g/m$^2$ SAP

TABLE 3

Adhesive/Application Pattern Comparison SAP Attachment to Pattern
"HWS" Tissue to Release Paper - For "SAP attachment" Testing*

| Examples | Adhesive | Application | Add-On (gm/m²) | "Superabsorbent Bonding" grams/.01 m²) | | | | | | | | | | AVE | STD |
|---|---|---|---|---|---|---|---|---|---|---|---|---|---|---|---|
| | | | | 1 | 2 | 3 | 4 | 5 | 6 | 7 | 8 | 9 | 10 | | |
| A1 | phobic | Spiral | 4 | 0.08 | 0.07 | 0.08 | 0.06 | 0.05 | 0.09 | 0.08 | 0.07 | 0.08 | 0.08 | 0.07 | 0.01 |
| A3 | phobic | Control Coat | 4 | 0.32 | 0.39 | 0.35 | 0.41 | 0.36 | 0.36 | 0.38 | 0.38 | 0.35 | 0.36 | 0.37 | 0.03 |
| A7 | phobic | Control Weave | 4 | 0.27 | 0.21 | 0.25 | 0.21 | 0.20 | 0.26 | 0.25 | 0.28 | 0.24 | 0.28 | 0.24 | 0.03 |
| B1 | H2561 | Spiral | 4 | 0.12 | 0.13 | 0.11 | 0.12 | 0.16 | 0.09 | 0.11 | 0.12 | 0.1 | 0.11 | 0.12 | 0.02 |
| B3 | H2561 | Control Coat | 4 | 0.45 | 0.49 | 0.52 | 0.44 | 0.48 | 0.46 | 0.45 | 0.45 | 0.46 | 0.48 | 0.47 | 0.02 |
| B7 | H2561 | Control Weave | 4 | 0.21 | 0.27 | 0.28 | 0.31 | 0.20 | 0.24 | 0.22 | 0.24 | 0.23 | 0.26 | 0.25 | 0.03 |
| C1 | H2594 | Spiral | 4 | 0.12 | 0.12 | 0.11 | 0.14 | 0.09 | 0.14 | 0.11 | 0.10 | 0.12 | 0.09 | 0.11 | 0.02 |
| C3 | H2594 | Control Coat | 4 | 0.40 | 0.42 | 0.42 | 0.41 | 0.40 | 0.36 | 0.36 | 0.40 | 0.45 | 0.44 | 0.41 | 0.03 |
| C7 | H2594 | Control Weave | 4 | 0.18 | 0.21 | 0.21 | 0.16 | 0.15 | 0.21 | 0.18 | 0.21 | 0.23 | 0.22 | 0.20 | 0.03 |

One example of the performance benefits of the folded absorbent core is illustrated by the Table 4 below.

TABLE 4

DIAPER PERFORMANCE

| | Strike-Through Time (Sec) | | |
|---|---|---|---|
| Diaper Type | 1st dose | 2nd dose | 3rd dose |
| Folded Absorbent Laminate | 38 | 41 | 36 |
| Conventional Pulp/SAP | 48 | 66 | 83 |

Table 4 describes the strike-through times for multiple doses of synthetic urine using a standard EDANA (European Disposables and Non-Wovens Association) test method. In the case of the conventional pulp/SAP core, strike through times increase significantly for multiple doses. On the other hand, for a diaper containing the folded absorbent core of the present invention, strike-through times remained lower than that of the first strike-through time for the conventional core, and remained substantially constant for three 100 ml doses of synthetic urine. This is believed to be due at least in part to the folded geometry of the absorbent core of the present invention.

Figure 16:
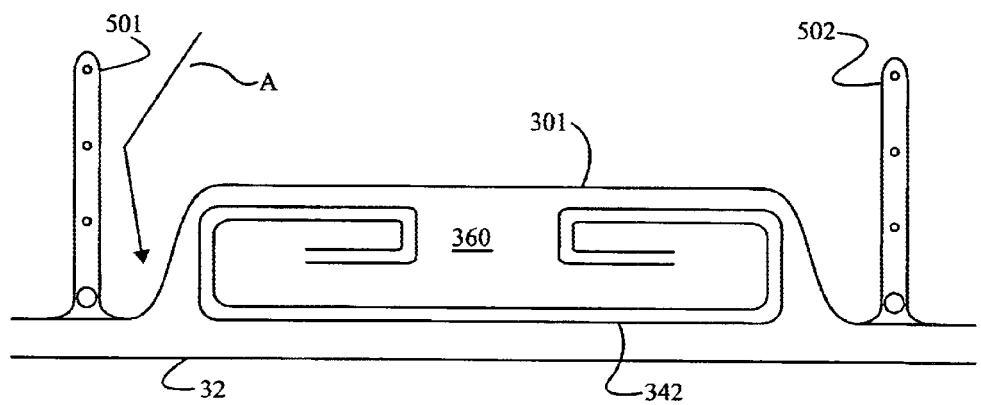
FIG. 16 is a cross-sectional schematic of a further preferred absorbent garment similar to that shown in FIG. 2.

With reference to FIG. 16, there is illustrated another preferred embodiment of a diaper construction employing the absorbent core described above. FIG. 16 is a cross-section similar to that shown in FIG. 2. In the embodiment of FIG. 16, the top sheet 301 extends substantially entirely across the width of the absorbent garment. A pair of unitary leg gathers 501, 502 are attached to the topsheet 301 outboard of the absorbent core 342. The unitary leg gathers 501, 502 are constructed with a plurality of elastic elements contained within a folded portion thereof. The lowermost elastic element preferably has an elastic restraining force which is greater than that of the elastic elements thereabove. Consequently, the lowermost elastic element may optionally entirely replace outboard leg elastics.

By placing the unitary leg gathers 501, 502 of FIG. 16 outboard of the absorbent core, it is believed that liquid containment is enhanced by causing laterally flowing liquid to be directed generally as shown by the arrow A into a crease formed between the unitary leg gathers 501, 502 and the side of the absorbent core 342. This flow of fluid complements the traditional migration of fluid into channel 360 to achieve optimum containment and dispersion of fluid within the absorbent core 342.

Figure 17:
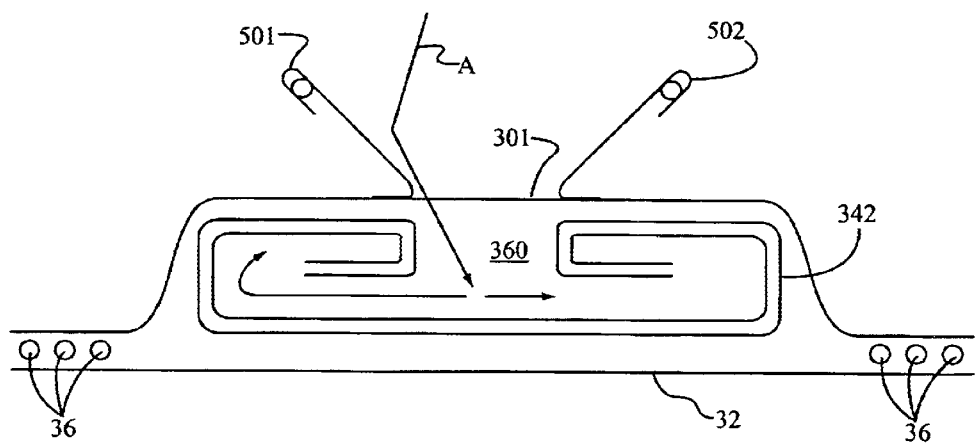
FIG. 17 is a cross-sectional schematic of a further preferred embodiment similar to that illustrated in FIG. 2.

With reference to FIG. 17, there is illustrated another preferred embodiment of an absorbent garment incorporating the absorbent core as described previously. In this embodiment, a pair of inboard leg gathers 501, are attached to unitary topsheet 301 above absorbent core 342. Outboard leg elastics 36 complement the leakage protection provided by the inboard leg gathers 501, 502 to provide a second barrier against the lateral flow of bodily waste. The inboard leg gathers 501, 502 are preferably positioned above respective sides of channel 360. This configuration is believed to cause liquid to be directed generally in the direction of arrow A, which as depicted is directly into channel 360. From there, the liquid is believed to migrate laterally outwardly and be contained generally within absorbent core 342. As will be readily appreciated by those of ordinary skill in the art, other diaper construction employing the absorbent core 342 of the preferred embodiments are within the scope of the invention as defined by the appended claims.

One exemplary embodiment of the thin absorbent core made from a folded absorbent laminate includes a C-folded absorbent laminate which has a central channel area, two side marginal areas, a front edge and a back edge. The two side folded marginal areas are C-folded at least once. This configuration forms two side-folded areas and a central channel area. The central channel area is believed to provide a free volume for containing liquid temporarily until the liquid can be absorbed by the absorbent laminate.

The fibrous layer of the absorbent layer preferably has a basis weight of about 40 g/sm and includes SAP having a basis weight of about 160 g/sm. In a most preferred embodiment, about 120 g/sm of the SAP is attached to the lower layer (e.g., the lower tissue layer) and about 40 g/sm of the SAP is loosely contained within the fibers of the fibrous layer.

The lower layer may be formed of a material having a basis weight of about 22 g/sm. Adhesive is preferably applied to the central portion of the lower layer at about 2–8 g/sm to achieve a liquid porosity for the central portion of the lower layer of less than about 10 ml/cm²/min. The outer portions of the lower layer are preferably about 38 mm wide and have adhesive applied to the outer portions at an adhesive application rate of about 2–5 g/sm to achieve a liquid porosity of greater than about 15 ml/cm²/min. The layers of the fibers are preferably attached to the upper layer by applying an adhesive at a basis weight of less than about 2 g/sm to maintain a liquid porosity of the upper layer of greater than about 40 ml/cm²/min.

The adhesive for attaching the SAP and fibers to the upper and lower layers is preferably a hydrophilic hot melt adhesive having an air/water advancing contact angle of less than about 30°.

Figure 18:
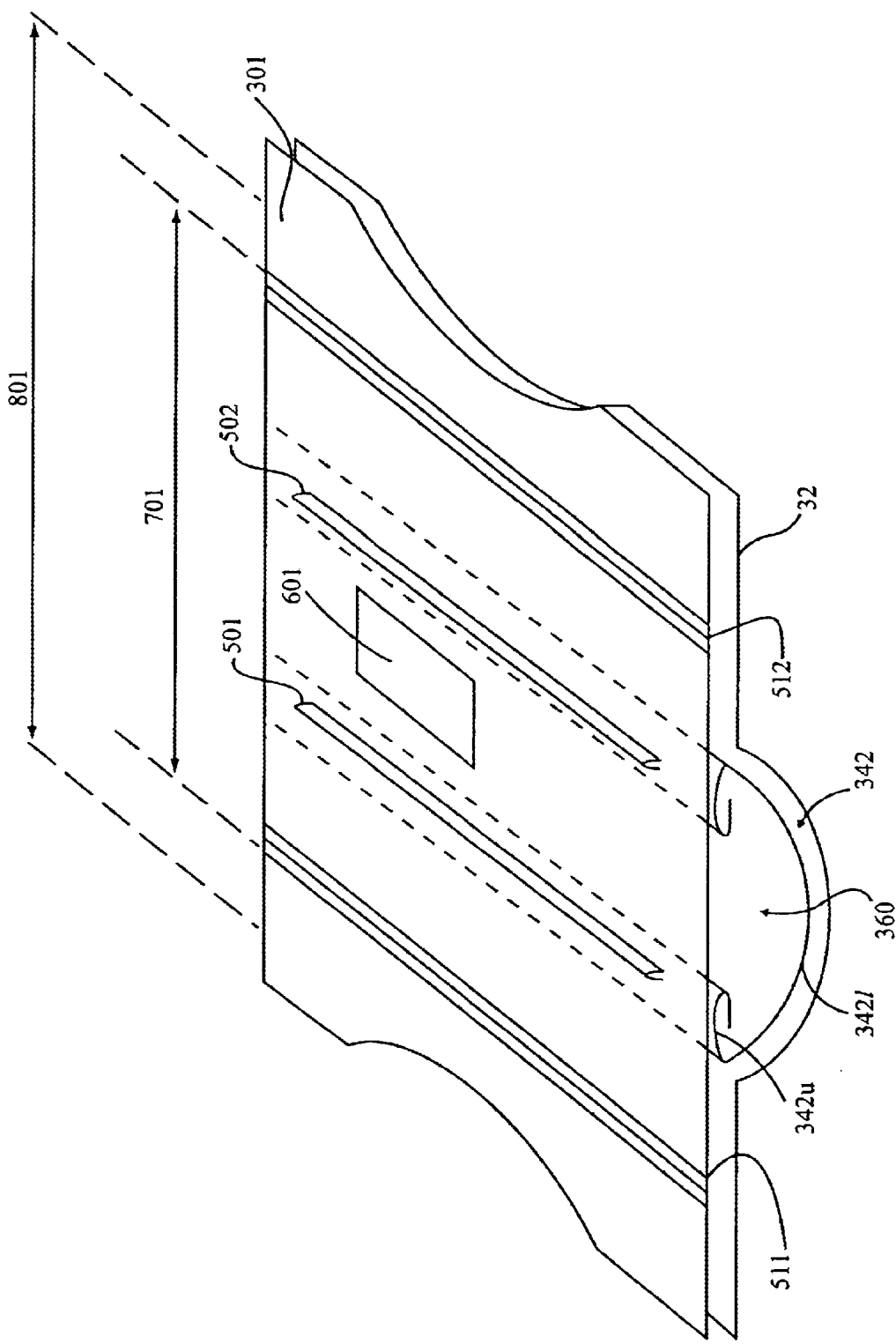
FIG. 18 is a schematic of a further preferred embodiment.

With reference to FIG. 18, there is illustrated a preferred embodiment of an absorbent garment incorporating the C-folded absorbent core as described previously. The illustrated absorbent garment is particularly configured to allow for improved bowel movement (BM) isolation and containment within the absorbent core and away from the user's skin. As shown, upper portions 342u of absorbent core 342 may be attached to topsheet 301 and lower portion 342l may be attached to backsheet 32 such that a central channel 360 is formed in the crotch region of the diaper when it is worn by an intended user. Of course it should be understood that absorbent core 342 may be attached to topsheet 301 or backsheet 32 directly or indirectly through intermediate optional laminates or layers (not shown).

Opening 601 is provided in topsheet 301 to allow BM to fill the central channel 360 formed by the absorbent core 342. As is apparent to one of ordinary skill in the art, opening 601 should be positioned so as to enable effective passage of BM through the topsheet 301 when the absorbent garment is worn by an intended user. Leg gathers 501 and 502 are positioned above the central channel 360 formed by absorbent core 342 to direct the movement of BM to opening 601 in topsheet 301. BM that passes through opening 601 in topsheet 301, moves forward in the absorbent garment, and will be separated form the skin of the intended user by the upper portions 342u of absorbent core 342 and topsheet 301. While not wishing to be bound by theory, it is believed that the swelling of upper portions 342u of folded, adhesively bonded absorbent core 342 may help to provide free volume in central channel 360 formed by absorbent core 342 below topsheet 301.

Free volume in central channel 360 may also be provided by laminating a narrower (flat) topsheet 301 to a wider (curved) backsheet 32 (with a partially attached absorbent core) using a laminating drum that has a longitudinal pocket or depression in the central region of the drum to impart curvature to the backsheet 32/core 342 assembly during lamination the topsheet 301.

Figure 20:
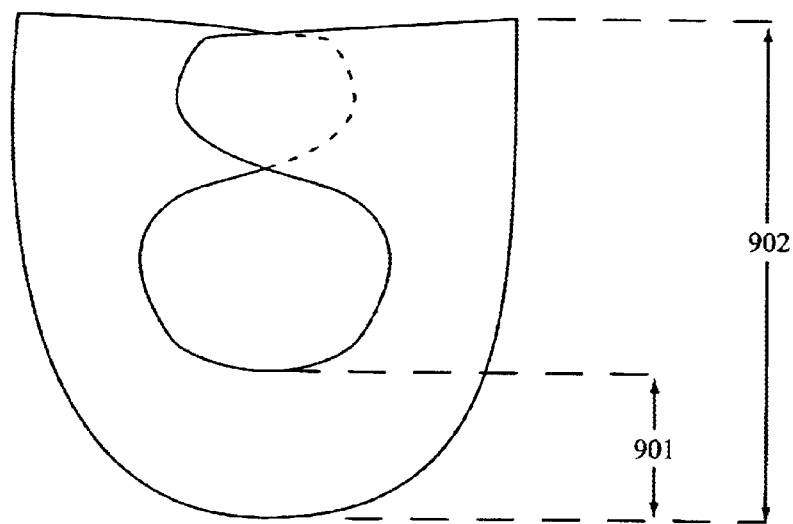
FIG. 20 is a side view of a preferred embodiment similar to that illustrated in FIG. 18 in an assembled state, as worn by an intended user.

Free volume in central channel 360 may also be provided in the absorbent garment by increasing the width 701 of the placement of leg elastics 511 and 512 and the crotch width 801 of the absorbent garment provided by the leg cut out. Generally, the width 801 is only slightly greater than the width 701. When the absorbent garment is worn, free volume in central channel 360 increases as the width 701 is increased. This is a result of the relatively fixed width of the spacing between an infant's legs and the tendency of the unattached (in the central region) topsheet 301 to buckle and remain close to the infant's skin. As width 701 in FIG. 18 is increased, the depth 901 of the fitted absorbent garment in FIG. 20 increases proportionally to provide increased free volume in central channel 360. Also, as width 701 is increased, it may be necessary to increase the length of the fitted diaper 902 to provide proper waist fit.

Figure 19:
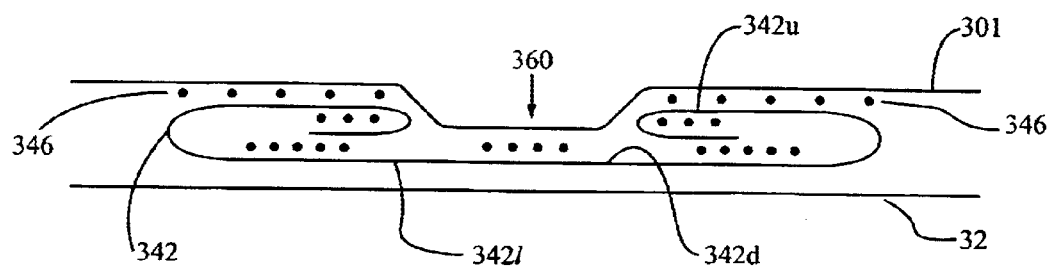
FIG. 19 is a cross-sectional schematic of a further preferred embodiment similar to that illustrated in FIG. 18.

As illustrated in FIG. 19, upper 342u and lower 3421 sections of absorbent core 342 can be bonded with adhesive 346 at the back end, or alternatively at both ends, of the core to prevent the flow of runny BM from the end of the absorbent garment. In addition, topsheet 301 at either end of the absorbent garment can be bonded to the bottom open side edges 342d of the central channel 360. Further, adhesive 346 can be applied intermittently to the bottom open side edges 342d of the central channel 360 in the middle of the absorbent garment to provide for the desired geometry and fit of the absorbent garment. An additional nonwoven or tissue (not-shown) can also optionally be folded with absorbent core 342 to provide for additional containment of SAP within absorbent core 342 and thereby prevent SAP from escaping through opening 601 formed in topsheet 301.

The invention has been described in connection with the preferred embodiments. These embodiments, however, are merely illustrative and the invention is not restricted thereto. It will be understood by those skilled in the art that other variations and modifications can easily be made within the scope of the invention as defined by the appended claims.

What is claimed:

1. An absorbent article comprising:
    a liquid permeable topsheet with an opening positioned so as to allow for passage of a bowel movement from an intended user through the topsheet;
    a backsheet; and
    an absorbent core positioned between the topsheet and the backsheet; wherein
        said absorbent core comprises a longitudinally C-folded absorbent laminate, said absorbent laminate comprising an upper layer, a lower layer, and an absorbent layer positioned between the upper and lower layers; wherein
        said C-folded absorbent laminate is folded to include a central channel area, two side marginal areas, a front edge and a back edge and wherein said two side marginal areas are C-folded at least once, forming two side folded areas and a central channel area, said central channel providing free volume wherein
            said free volume provides for containment of bowel movements which have passed though the opening in said topsheet, and provides for containment of liquid temporarily until the liquid can be absorbed by the absorbent laminate.

2. The absorbent article of claim 1 wherein said absorbent layer comprises from about 50 to about 95 percent by weight SAP.

3. The absorbent article of claim 1, wherein the folded width of said C-folded absorbent laminate is about 110–130 mm and includes a central channel area, two side marginal areas, a front edge and a back edge and wherein said two side marginal areas are C-folded at least once, forming two side folded areas having a width of about 20–40 mm each and a central channel area having a width of about 50–70 mm, wherein said central channel provides free volume for containing liquid temporarily until the liquid can be absorbed by the absorbent laminate.

4. The absorbent article of claim 3, further comprising a pair of inner waste flaps positioned on the diaper topsheet so as to contain and direct the flow of urine to said central channel in the absorbent core.

5. The absorbent article of claim 1, wherein said absorbent core contains a full- or partial-length internal spreading layer, said spreading layer selected from the group consisting of high bulk tissue, airlaid nonwoven, and synthetic high loft nonwoven.

6. The absorbent article of claim 5, said high bulk tissue layer having a basis weight of about 15–40 g/sm, said airlaid nonwoven having a basis weight of about 35–100 g/sm and said synthetic high loft nonwoven having a basis weight of about 20–80 g/sm.

7. The absorbent article of claim 1, wherein said absorbent laminate has a thickness of about 0.5–1.1 mm.

8. The absorbent article of claim 1, wherein the upper and lower layers are made from materials selected from the groups consisting of tissue having a basis weight of about 10–40 g/sm, airlaid fluff pulp having a basis weight of about 35–100 g/sm, and synthetic nonwoven having a basis weight of about 15–25 g/sm.

9. The absorbent article of claim 1, wherein the upper layer has a porosity greater than about 40 ml/cm$^2$/min, and the lower layer has a machine directional wet tensile strength greater than about 200 gm/inch.

10. The absorbent article of claim 2, wherein said absorbent layer further comprises a layer of fibers, a portion of said layer of fibers being bound to both said upper and lower layers, and wherein a portion of said SAP material is adhesively bound to the bottom layer while another portion of said SAP material is loosely contained within said fibers of the absorbent layer.

11. The absorbent article of claim 10, said fibrous layer of said absorbent layer having a basis weight of about 40 g/sm and said SAP having a basis weight of about 160 g/sm.

12. The absorbent article of claim 11, wherein about 120 g/sm of SAP is attached to said lower layer and about 40 g/sm of SAP is loosely contained within said fibers.

13. The absorbent article of claim 10, wherein said SAP material is bound to a central portion of the lower layer by applying an adhesive at a relatively high coverage along the central portion of the lower layer, said adhesive decreasing the porosity of the central portion of the lower layer; and wherein additional SAP is bound to outer portions of the lower layer by applying an adhesive at an intermediate coverage to maintain porosity in the outer portions of the lower layer; and wherein said layer of fibers is bound to the upper layer by applying an adhesive at a relatively lower coverage to maintain a highly liquid porous structure of the upper layer.

14. The absorbent article of claim 13, wherein said lower layer has a basis weight of about 22 g/sm, said central portion of said lower layer is about 125 mm, and said adhesive is applied to said central portion at about 2 to 8 g/sm, to achieve a liquid porosity for said central portion of the lower layer of less than about 10 ml/cm$^2$/min; and wherein said outer portions of said lower layer are about 38 mm, said adhesive applied to said outer portions of said lower layer at about 2–5 g/sm, to achieve a liquid porosity of greater than about 15 ml/cm$^2$/min.; and wherein said layer of fibers is attached to the upper layer by applying an adhesive at a basis weight of less than about 2 g/sm to maintain a liquid porosity of the upper layer of greater than about 40 ml/cm$^2$/min.

15. The absorbent article of claim 10, wherein the adhesive is a hydrophilic hot melt adhesive having an air/water advancing contact angle of less than about 30°.

16. The absorbent article of claim 10, wherein said layer of fibers is a tow of cellulose acetate or polypropylene fibers.

17. The absorbent article of claim 10, wherein said layer of fibers comprises polypropylene fibers formed by meltblown or DYNAFIBER™ UFD polymer spray nozzles.

18. The absorbent article of claim 10, wherein said absorbent layer comprises fibers selected from the group consisting of cellulose acetate fibers, rayon fibers, lyocell fibers, polyacrylonitrile fibers, cotton fibers, cotton linters, and blends thereof.

19. The absorbent article of claim 10, wherein said absorbent layer comprises fibers selected from the group consisting of surface modified polyester fibers, surface-modified polyolefin/polyester bicomponent fibers, surface-modified polyester/polyester bicomponent fibers, and blends thereof.

20. The absorbent article of claim 10, wherein said layer of fibers is a tow of cellulose acetate fibers, polypropylene fibers, polyester fibers, rayon fibers, lyocell fibers, polyacrylonitrile fibers, cotton fibers, cotton linters or blends thereof.

21. The absorbent article of claim 2, wherein the absorbent layer has a basis weight of 100 to 400 g/sm.

22. The absorbent article of claim 21, said upper layer comprising a tissue layer having a basis weight of about 16 g/sm, said lower layer comprising a tissue layer having a basis weight of about 22 g/sm, wherein the absorbent layer has a fiber basis weight of about 40 g/sm and a SAP basis weight of about 120 g/sm.

23. The absorbent article of claim 1, said upper layer comprising a tissue layer having a basis weight of about 16 g/sm, said lower layer comprising a tissue layer having a basis weight of about 22 g/sm, wherein the absorbent layer has a fiber basis weight of about 40 g/sm and a SAP basis weight of about 160 g/sm.

24. The absorbent article of claim 2, wherein said SAP has an FVAUL greater than about 15 cm$^3$/60 ml.

25. The absorbent article of claim 2, wherein said absorbent layer further comprises about 5 to about 50 percent by weight fibrous or particulate non-SAP additives.

26. The absorbent article of claim 2, wherein said absorbent layer further comprises up to about 20 percent by weight fluff wood pulp fibers.

27. The absorbent article of claim 2, wherein said absorbent layer further comprises up to about 5 percent by weight thermally bondable fibers.

28. The absorbent article of claim 2, wherein the absorbent layer further comprises particulate additives.

29. The absorbent article of claim 28, wherein said particulate additives comprise insoluble, hydrophilic polymers with particle diameters of 100 μm or less.

30. The absorbent article of claim 29, wherein said particulate additives are selected from the group consisting of potato, corn, wheat, partially cooked starches and rice starches.

31. The absorbent article of claim 28, wherein said particulate additives comprise insoluble, dried beet fiber or other vegetable or fruit by-products.

32. The absorbent article of claim 1, further comprising a transfer layer positioned between said topsheet and said upper layer, said transfer layer adhesively secured to said upper layer and to said topsheet.

33. The absorbent article of claim 2, wherein said SAP has a particle size distribution comprised of particles having particle diameters up to about 600 μm.

* * * * *